United States Patent
Liang

(10) Patent No.: US 7,691,815 B2
(45) Date of Patent: Apr. 6, 2010

(54) METHODS FOR BLOCKING TNF-ALPHA ACTIVITY IN MAMMALS WITH TRIMERIC SOLUBLE TNF RECEPTORS

(75) Inventor: Peng Liang, Nashville, TN (US)

(73) Assignee: Gen Hunter Corporation, Nashville, TN (US)

( * ) Notice: Subject to any disclaimer, the term of this patent is extended or adjusted under 35 U.S.C. 154(b) by 290 days.

(21) Appl. No.: 11/643,285

(22) Filed: Dec. 21, 2006

(65) Prior Publication Data

US 2007/0117755 A1    May 24, 2007

Related U.S. Application Data

(63) Continuation-in-part of application No. 10/677,877, filed on Oct. 2, 2003, now Pat. No. 7,268,116.

(51) Int. Cl.
*A61K 38/00* (2006.01)

(52) U.S. Cl. .................................................. 514/12

(58) Field of Classification Search .................. None
See application file for complete search history.

(56) References Cited

FOREIGN PATENT DOCUMENTS

WO    WO 97/17988    *    5/1997

* cited by examiner

*Primary Examiner*—Lisa J Hobbs
(74) *Attorney, Agent, or Firm*—Lambert & Associates; Adam J. Bruno; Gary E. Lambert

(57) ABSTRACT

This invention relates to a general methodology for efficient creation of trimeric soluble receptors for therapeutic applications. The process involves gene fusion between a soluble receptor with a ligand binding domain and a trimerization tag from the C-propeptide domain of pro-collagen, which is capable of self-assembly into a covalently linked trimer. Using both in vitro bioassays and an in vivo mouse model for collagen-induced arthritis (CIA), we show that the homotrimeric soluble TNF receptor produced with such method is a more potent blocker than dimeric TNF receptor decoys in inhibiting TNF-α mediated inflammatory diseases.

13 Claims, 6 Drawing Sheets

Figure 2A:
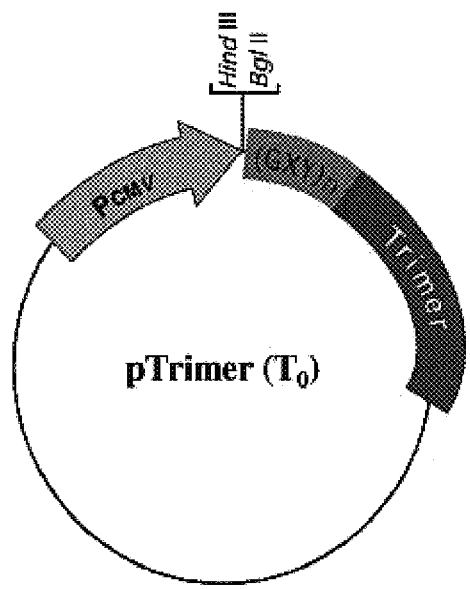

Side-View
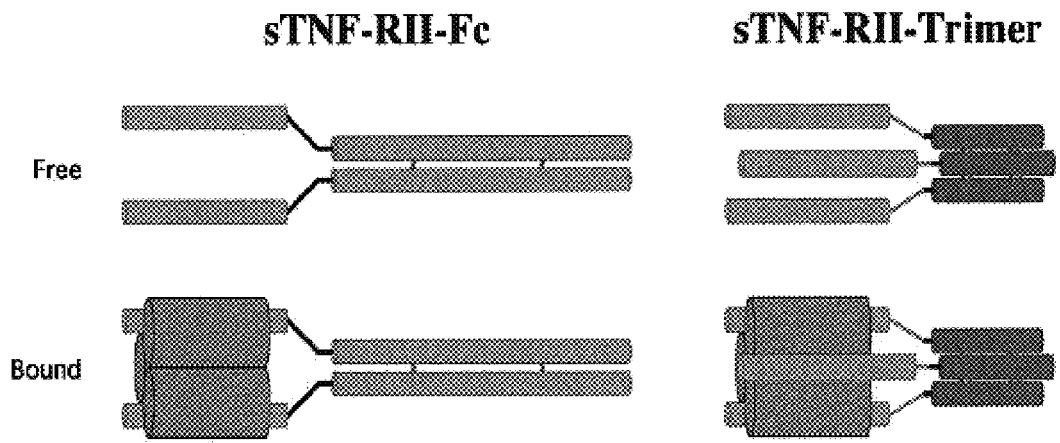
FIG. 1A
FIG. 1C
Top-View
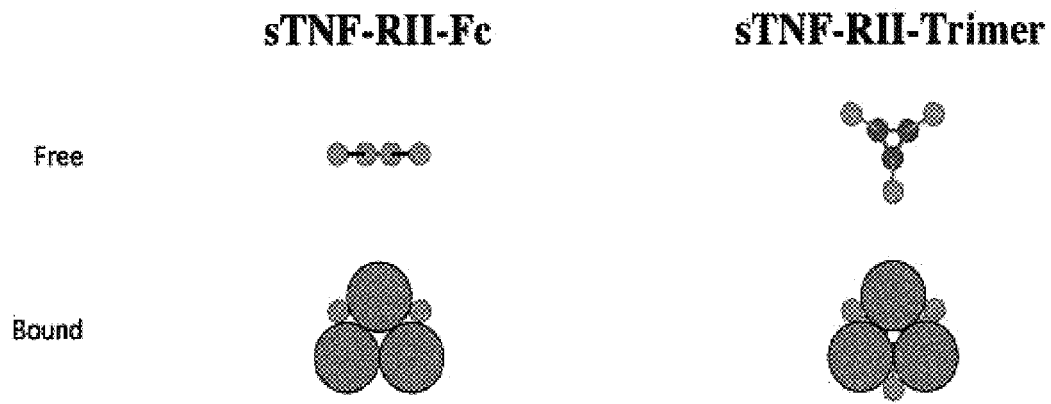
FIG. 1B
FIG. 1D

A

B

METHODS FOR BLOCKING TNF-ALPHA ACTIVITY IN MAMMALS WITH TRIMERIC SOLUBLE TNF RECEPTORS

CROSS REFERENCE TO RELATED APPLICATION

This application is a continuation-in-part of prior U.S. application Ser. No. 10/677,877 filed on Oct. 2, 2003, now U.S. Pat. No. 7,268,116.

FIELD OF THE INVENTION

The present invention relates to methods for protein expression, and more specifically, for creating and expressing secreted and biologically active trimeric proteins, such as trimeric soluble receptors.

BACKGROUND OF INVENTION

In multicellular organisms, such as humans, cells communicate with each other by the so-called signal transduction pathway, in which a secreted ligand (e.g. cytokines, growth factors or hormones) binds to its cell surface receptor(s), leading to receptor activation. The receptors are membrane proteins, which consist of an extracellular domain responsible for ligand binding, a central transmembrane region followed by a cytoplasmic domain responsible for sending the signal downstream. Signal transduction can take place in the following three ways: paracrine (communication between neighboring cells), autocrine (cell communication to itself) and endocrine (communication between distant cells through circulation), depending on the source of a secreted signal and the location of target cell expressing a receptor(s). One of the general mechanisms underlying receptor activation, which sets off a cascade of events beneath the cell membrane including the activation of gene expression, is that a polypeptide ligand such as a cytokine, is present in an oligomeric form, such as a homo- dimer or trimer, which when bound to its monomeric receptor at the cell outer surface, leads to the oligomerization of the receptor. Signal transduction pathways play a key role in normal cell development and differentiation, as well as in response to external insults such as bacterial and viral infections. Abnormalities in such signal transduction pathways, in the form of either underactivation (e.g. lack of ligand) or overactivation (e.g. too much ligand), are the underlying causes for pathological conditions and diseases such as arthritis, cancer, AIDS, and diabetes.

One of the current strategies for treating these debilitating diseases involves the use of receptor decoys, such as soluble receptors consisting of only the extracellular ligand-binding domain, to intercept a ligand and thus overcome the overactivation of a receptor. The best example of this strategy is the creation of Enbrel®, a dimeric soluble TNF-α receptor-immunoglobulin (IgG) fusion protein by Immunex (Mohler et al., 1993; Jacobs et al., 1997), which is now part of Amgen. The TNF family of cytokines is one of the major pro-inflammatory signals produced by the body in response to infection or tissue injury. However, abnormal production of these cytokines, for example, in the absence of infection or tissue injury, has been shown to be one of the underlying causes for diseases such as arthritis and psoriasis. Naturally, a TNF-α receptor is present in monomeric form on the cell surface before binding to its ligand, TNF-α, which exists, in contrast, as a homotrimer (Locksley et al., 2001). Accordingly, fusing a soluble TNF-α receptor with the Fc region of immunoglobulin G1, which is capable of spontaneous dimerization via disulfide bonds (Sledziewski et al., 1992 and 1998), allowed the secretion of a dimeric soluble TNF-α receptor (Mohler et al., 1993; Jacobs et al., 1997). In comparison with the monomeric soluble receptor, the dimeric TNF-α receptor II -Fc fusion has a greatly increased affinity to the homo-trimeric ligand. This provides a molecular basis for its clinical use in treating rheumatoid arthritis (RA), an autoimmune disease in which constitutively elevated TNF-α, a major pro-inflammatory cytokine, plays an important causal role. Although Enbrel® was shown to have a Ki in the pM range (ng/mL) to TNF-α (Mohler et al., 1993), 25 mg twice a week subcutaneous injections, which translates to µg/mL level of the soluble receptor, are required for the RA patients to achieve clinical benefits (www.enbrel.com). The high level of recurrent Enbrel® consumption per RA patients has created a great pressure as well as high cost for the drug supply, which limits the accessibility of the drug to millions of potential patients in this country alone.

In addition to the TNF-α family of potent proinflammatory cytokines, the HIV virus that causes AIDS also uses a homo-trimeric coat protein, gp120, to gain entry into CD-4 positive T helper cells in our body (Kwong et al., 1998). One of the earliest events during HIV infection involves the binding of gp120 to its receptor CD-4, uniquely expressed on the cell surface of T helper cells (Clapham et al., 2001). Monomeric soluble CD-4 was shown over a decade ago as a potent agent against HIV infection (Clapham et al., 1989) however, the excitement was sadly dashed when its potency was shown to be limited only to laboratory HIV isolates (Daar et al., 1990). It turned out that HIV strains from AIDS patients, unlike the laboratory isolates, had a much lower affinity to the monomeric soluble CD-4, likely due to the sequence variation on the gp120 (Daar et al., 1990). Although the dimeric soluble CD-4-Fc fusion proteins have been made, these decoy CD-4 HIV receptors showed little antiviral effect against natural occurring HIVs from AIDS patients, both in the laboratories and in clinics, due to the low affinity to the gp120 (Daar et al., 1990).

Clearly, there is a great need to be able to create secreted homo-trimeric soluble receptors or biologically active proteins, which can have perfectly docked binding sites, hence higher affinity, to their naturally occurring homo-trimeric ligands, such as the TNF family of cytokines and HIV coat proteins. Such trimeric receptor decoys theoretically should have a much higher affinity than its dimeric counterparts to their trimeric ligand. Such rationally designed soluble trimeric receptor analogs could significantly increase the clinical benefits as well as lower the amount or frequency of the drug injections for each patient. To be therapeutically feasible, a desired trimerizing protein moiety for biologic drug designs should satisfy the following criteria. Ideally it should be part of a naturally secreted protein, like immunoglobulin Fc, that is also abundant (non-toxic) in the circulation, human in origin (lack of immunogenicity), relatively stable (long half-life), capable of efficient self-trimerization which is strengthened by inter-chain covalent disulfide bonds, and pertain an optimal geometry in projecting soluble receptor to be trimerized to confirm maximum ligand binding.

Collagen is a family of fibrous proteins that are the major components of the extracellular matrix. It is the most abundant protein in mammals, constituting nearly 25% of the total protein in the body. Collagen plays a major structural role in the formation of bone, tendon, skin, cornea, cartilage, blood vessels, and teeth (Stryer, 1988). The fibrillar types of collagen I, II, III, IV, V, and XI are all synthesized as larger trimeric precursors, called procollagens, in which the central uninterrupted triple-helical domain consisting of hundreds of "G-X-Y" repeats (or glycine repeats) is flanked by non-collagenous domains (NC), the N-propeptide and the C-propeptide (Stryer, 1988). Both the C- and N-terminal extensions are processed proteolytically upon secretion of the procollagen, an event that triggers the assembly of the mature protein into collagen fibrils which forms an insoluble cell matrix (Prockop et al., 1998). BMP-1 is a protease that recognizes a specific peptide sequence of procollagen near the junction between the glycine repeats and the C-prodomain of collagens and is responsible for the removal of the propeptide (Li et al.). The shed trimeric C-propeptide of type I collagen is found in human sera of normal adults at a concentration in the range of 50-300 ng/mL, with children having a much higher level which is indicative of active bone formation (Melkko et al.). In people with familial high serum concentration of C-propeptide of type I collagen, the level could reach as high as 1-6 µg/mL with no apparent abnormality, suggesting the C-propeptide is not toxic (Sorva et al.). Structural study of the trimeric C-propeptide of collagen suggested that it is a tri-lobed structure with all three subunits coming together in a junction region near their N-termini to connect to the rest of the procollagen molecule (Bernocco et al.). Such geometry in projecting proteins to be fused in one direction is similar to that of Fc dimer.

Type I, IV, V and XI collagens are mainly assembled into heterotrimeric forms consisting of either two α-1 chains and one α-2 chain (for Type I, IV, V), or three different a chains (for Type XI), which are highly homologous in sequence. The type II and III collagens are both homotrimers of α-1 chain. For type I collagen, the most abundant form of collagen, stable α1(I) homotrimer is also formed and is present at variable levels (Alvares et al., 1999) in different tissues. Most of these collagen C-propeptide chains can self-assemble into homotrimers, when over-expressed alone in a cell. Although the N-propeptide domains are synthesized first, molecular assembly into trimeric collagen begins with the in-register association of the C-propeptides. It is believed the C-propeptide complex is stabilized by the formation of interchain disulfide bonds, but the necessity of disulfide bond formation for proper chain registration is not clear. The triple helix of the glycine repeats and is then propagated from the associated C-termini to the N-termini in a zipper-like manner. This knowledge has led to the creation of non-natural types of collagen matrix by swapping the C-propeptides of different collagen chains using recombinant DNA technology (Bulleid et al., 2001). Non-collagenous proteins, such as cytokines and growth factors, also have been fused to the N-termini of either pro-collagens or mature collagens to allow new collagen matrix formation, which is intended to allow slow release of the noncollagenous proteins from the cell matrix (Tomita et al., 2001). However, under both circumstances, the C-propeptides are required to be cleaved before recombinant collagen fibril assembly into an insoluble cell matrix.

Although, other protein trimerization domains, such as those from GCN4 from yeast (Yang, X. et al, 2000), fibritin from bacteria phage T4 (Frank, S. et al., 2001) and aspartate transcarbamoylase of *Escherichia coli* (Chen, B. et al., 2004), have been described previously to allow trimerization of heterologous proteins, none of these trimerizing proteins are human in nature, nor are they naturally secreted proteins. As such, any trimeric fusion proteins would have to be made intracellularly, which not only may fold incorrectly for naturally secreted proteins such as soluble receptors, but also make purification of such fusion proteins from thousands of other intracellular proteins difficult. Moreover, the fatal drawback of using such non-human protein trimerization domains (e.g. from yeast, bacteria phage and bacteria) for trimeric biologic drug design will be their immunogenicity in the human body, rendering such fusion proteins ineffective within weeks after injecting into the human body.

One secreted protein previously used as a protein trimerization tag is tetranectin, which is a plasminogen-binding protein of C-lectin family (Holtet et al.). However, unlike IgG Fc dimerization tag, the trimeric tetranectin structure is not strengthened by any interchain disulfide bonds, and significant fractions of both monomeric and dimeric tetranectin co-existed with the trimeric structure in solution (Holtet et al.). Physiologically, teranectin is involved in tissue remodeling and increased cell matrix concentration of tetranectin in human has been linked to multiple cancer types. Recombinant heterologous tetranectin fusion proteins have only been produced intracellularly in *E. coli* as insoluble inclusion bodies that required refolding to obtain soluble structures (Holtet et al. and Graversen et al.). These unfavorable attributes suggest that tetranectin is not ideal for therapeutic applications as a protein trimerization tag. Nonetheless, bacterially produced ApoAI-Tetranectin fusion protein has been produced and patented (Graversen et al.) and is being tested as a therapeutic agent for atherosclerosis.

SUMMARY OF THE INVENTION

Disclosed here is an invention that allows any soluble receptors or biologically active polypeptides to be made into trimeric forms as secreted proteins. The essence of the invention is to fuse any soluble receptors and biologically active proteins in-frame to the C-propeptide domain of fibrillar collagen, which is capable of self-trimerization, using recombinant DNA technology. The resulting fusion proteins when expressed in eukaryotic cells are secreted as soluble proteins essentially 100% in trimeric forms covalently strengthened by inter-molecular disulfide bonds formed among three C-propeptides.

In one aspect of the invention, a method for producing secreted trimeric fusion proteins is disclosed, comprising the following: (a) introducing into a eukaryotic host cell a DNA construct comprising a promoter which drives the transcription of an open reading frame consisting of a signal peptide sequence which is linked in-frame to a non-collagen polypeptide to be trimerized, which in turn is joined in-frame to the C-terminal portion of collagen capable of self-trimerization; (b) growing the host cell in an appropriate growth medium under physiological conditions to allow the secretion of a trimerized fusion protein encoded by said DNA sequence; and (c) isolating the secreted trimeric fusion protein from a host cell.

Within one embodiment, the signal peptide sequence is the native sequence of the protein to be trimerized. Within another embodiment, the signal peptide sequence is from a secreted protein different from that to be trimerized. Within one embodiment, the non-collagen polypeptide to be trimerized is a soluble receptor consisting of the ligand binding domain(s). Within one embodiment, the C-terminal portion of collagen is the C-propeptide without any triple helical region of collagen (SEQ ID NOS: 3-4 and SEQ ID NOS: 17-18). Within another embodiment, the C-terminal collagen consists of a portion of the triple helical region of collagen as linker to the non-collagenous proteins to be trimerized (SEQ ID NOS. 1-2). Within another embodiment, the C-terminal portion of collagen has a mutated or deleted BMP-1 protease recognition site (SEQ ID NOS. 3-4 and SEQ ID NOS: 17-18).

In one aspect of the invention, a method for producing a secreted trimeric fusion protein is disclosed, comprising the following: (a) introducing into a eukaryotic host cell a DNA construct comprising a promoter which drives the transcription of an open reading frame consisting of a signal peptide sequence which is linked in-frame to a non-collagen polypeptide to be trimerized, which in turn is joined in-frame to the C-terminal portion of collagen capable of self-trimerization, selected from pro.alpha.1(I), pro.alpha.2(I), pro.alpha.1 (II), pro.alpha.1 (111), pro.alpha.1 (V), pro.alpha.2(V), pro.alpha.1(XI), pro.alpha.2(XI) and pro.alpha.3(XI); (b) growing the host cell in an appropriate growth medium under physiological conditions to allow the secretion of a trimerized fusion protein encoded by said DNA sequence; and (c) isolating the secreted trimeric fusion protein from a host cell.

In a preferred embodiment, the non-collagen polypeptide to be trimerized is the soluble TNF-RII (p75) (SEQ ID NOS. 9-12 and SEQ ID NOS. 19-20). In another preferred embodiment, the non-collagen polypeptide to be trimerized is soluble CD-4, the co-receptor of HIV (SEQ ID NOS. 13-16). In yet another preferred embodiment, the non-collagen polypeptide to be trimerized is a placental secreted alkaline phosphatase (SEQ ID NOS. 5-8).

In one aspect of the invention, a method for producing a secreted trimeric fusion protein is disclosed, comprising the following: (a) introducing into a eukaryotic host cell a first DNA construct comprising a promoter which drives the transcription of an open reading frame consisting of a signal peptide sequence which is linked in-frame to a non-collagen polypeptide to be trimerized, which in turn is joined in-frame to the C-terminal portion of collagen capable of self-trimerization, selected from pro.alpha.1 (1), pro.alpha.2(I), pro.alpha.1 (II), pro.alpha.1 (III), pro.alpha.1 (V), pro.alpha.2(V), pro.alpha.1(XI), pro.alpha.2(XI) and pro.alpha.3(XI); (b) introducing into a eukaryotic host cell a second DNA construct comprising a promoter which drives the transcription of an open reading frame consisting of a second signal peptide sequence which is linked in-frame to a second non-collagen polypeptide to be trimerized, which in turn is joined in-frame to the second C-terminal portion of collagen capable of self-trimerization, selected from pro.alpha.1(I), pro.alpha.2(I), pro.alpha.1(II), pro.alpha.1(III), pro.alpha.1(V), pro.alpha.2 (V), pro.alpha.1(XI), pro.alpha.2(XI) and pro.alpha.3(XI); (c) growing the host cell in an appropriate growth medium under physiological conditions to allow the secretion of a trimerized fusion protein encoded by said first and second DNA sequences; and (d) isolating the secreted trimeric fusion protein from the host cell.

In one aspect of the invention, a method for producing a secreted trimeric fusion protein is disclosed, comprising the following: (a) introducing into a eukaryotic host cell a first DNA construct comprising a promoter which drives the transcription of an open reading frame consisting of a signal peptide sequence which is linked in-frame to a non-collagen polypeptide to be trimerized, which in turn is joined in-frame to the C-terminal portion of collagen capable of self-trimerization, selected from pro.alpha.1(I), pro.alpha.2(I), pro.alpha.1(II), pro.alpha.1(III), pro.alpha.1 (V), pro.alpha.2(V), pro.alpha.1(XI), pro.alpha.2(XI) and pro.alpha.3(XI); (b) introducing into a eukaryotic host cell a second DNA construct comprising a promoter which drives the transcription of an open reading frame consisting of a second signal peptide sequence which is linked in-frame to a second non-collagen polypeptide to be trimerized, which in turn is joined in-frame to a second C-terminal portion of collagen capable of self-trimerization, selected from pro.alpha.1(I), pro.alpha.2(I), pro.alpha.1(II), pro.alpha.1(III), pro.alpha.1(V), pro.alpha.2 (V), pro.alpha.1(XI), pro.alpha.2(XI) and pro.alpha.3(XI); (c) introducing into a eukaryotic host cell a third DNA construct comprising a promoter which drives the transcription of an open reading frame consisting of a third signal peptide sequence which is linked in-frame to a third non-collagen polypeptide to be trimerized, which in turn is joined in-frame to a third C-terminal portion of collagen capable of self-trimerization, selected from pro.alpha.1 (I), pro.alpha.2(I), pro.alpha.1 (II), pro.alpha.1(III), pro.alpha.1(V), pro.alpha.2 (V), pro.alpha.1(XI), pro.alpha.2(XI) and pro.alpha.3(XI); (d) growing the host cell in an appropriate growth medium under physiological conditions to allow the secretion of a trimerized fusion protein encoded by said first and second DNA sequences; and (e) isolating the secreted trimeric fusion protein from the host cell.

The following are the advantages of this invention: (1) collagen is the most abundant protein secreted in the body of a mammal, constituting nearly 25% of the total proteins in the body; (2) the major forms of collagen naturally occur as trimeric helixes, with their globular C-propeptides being responsible for the initiating of trimerization; (3) the trimeric C-propeptide of collagen proteolytically released from the mature collagen is found naturally at sub microgram/mL level in the blood of mammals and is not known to be toxic to the body; (4) the linear triple helical region of collagen can be included as a linker with predicted 2.9 Å spacing per residue, or excluded as part of the fusion protein so the distance between a protein to be trimerized and the C-propeptide of collagen can be precisely adjusted to achieve an optimal biological activity; (5) the recognition site of BMP1 which cleaves the C-propeptide off the pro-collagen can be mutated or deleted to prevent the disruption of a trimeric fusion protein; (6) the C-propeptide domain provides a universal affinity tag, which can be used for purification of any secreted fusion proteins created by this invention.

In contrast to the Fc Tag technology (Sledziewski et al., 1992 and 1998), with which secreted dimeric fusion proteins can be created, this timely invention disclosed herein enables the creation and secretion of soluble trimeric fusion proteins for the first time. Given the fact that a homotrimer has 3-fold symmetry, whereas a homodimer has only 2-fold symmetry, the two distinct structural forms theoretically can never be perfectly overlaid (FIGS. 1A-1D). As such, neither the homodimeric soluble TNF-R-Fc (e.g., Enbrel®), nor the soluble CD4-Fc fusion proteins, could have had an optimal interface for binding to their corresponding homotrimeric ligands, TNF-α and HIV gp120, respectively. In contrast, homotrimeric soluble TNF receptors and CD4 created by the current invention are trivalent and structurally have the potential to perfectly dock to the corresponding homotrimeric ligands. Thus, these trimeric soluble receptor analogs can be much more effective in neutralizing the biological activities of their trimeric ligands. With this timely invention, more effective yet less expensive drugs, such as trimeric soluble TNF-R and CD4 described in the preferred embodiments, can be readily and rationally designed to combat debilitating diseases such as arthritis and AIDS. Trimeric soluble gp120 can also be created with this invention, which could better mimic the native trimeric gp120 coat protein complex found on HIV viruses, and used as a more effective vaccine compared to non-trimeric gp120 antigens previously used. Also chimeric antibodies in trimeric form can be created with the current invention, which could endow greatly increased avidity of an antibody in neutralizing its antigen.

BRIEF DESCRIPTION OF DRAWINGS AND SEQUENCE LISTINGS

FIG. 1A, FIG. 1B, FIG. 1C, and FIG. 1D is a schematic representation of the method according to the invention compared to prior dimeric immunoglobulin Fc fusion.

FIG. 1A is a side elevation view and FIG. 1B is a top plan view: Structural characteristics of a homodimeric soluble sTNF RII receptor-Fc fusion, such as Amgen's Enbrel®, in either ligand-free or -bound form as indicated.

Domains labeled in green denote soluble TNF-RII. Note that the Fc (labeled in light blue with inter-chain disulfide bonds in red) fusion protein is dimeric in structure. Given its 2-fold symmetry, the dimeric Fc fusion protein is bivalent and thus theoretically does not have the optimal conformation to bind to a homotrimeric ligand, such as TNF-α (labeled in brown), which has a 3-fold symmetry.

FIG. 1C is a side elevation view and FIG. 1D is a top plan view: Structural characteristics of a trimeric soluble sTNF RII receptor-C-propeptide fusion.

Given its 3-fold symmetry, a sTNF RII-Trimer fusion protein is trivalent in nature, thus can perfectly dock to its trimeric ligand TNF-α, C-propeptide of collagen capable of self trimerization is labeled in dark blue with inter-chain disulfide bonds labeled in red.

Figure 2B:
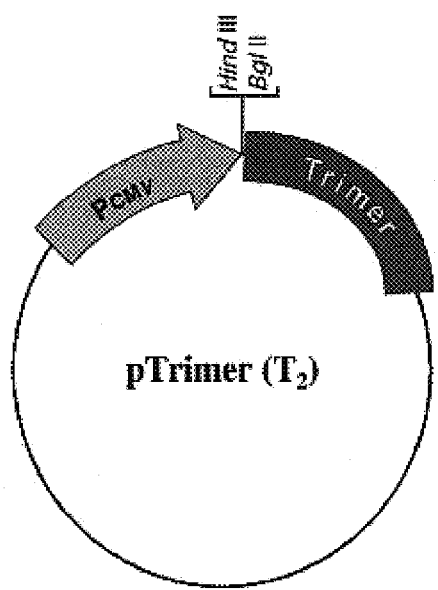

FIG. 2A and FIG. 2B schematic representation of pTRIMER expression vectors for creating secreted trimeric fusion proteins. Any soluble receptor- or biological active polypeptide-encoding cDNAs can be cloned into the unique Hind III or Bgl II sites to allow in-frame fusion at the C-termini to the α (I) collagen containing C-propeptide sequence for trimerization. FIG. 2A The pTRIMER(T0) construct contains part of the glycine-repeats (GXY)n upstream of the C-propeptide; FIG. 2B: whereas the pTRIMER(T2) contains only the C-propeptide domain with a mutated BMP-1 protease recognition site. pTRIMER(T3) has essentially the same structure as that of pTRIMER(T2).

FIGS. 3A, 3B, 3C and 3D illustrate the expression and secretion of disulfide bond-linked trimeric collagen fusion proteins.

Figure 3:
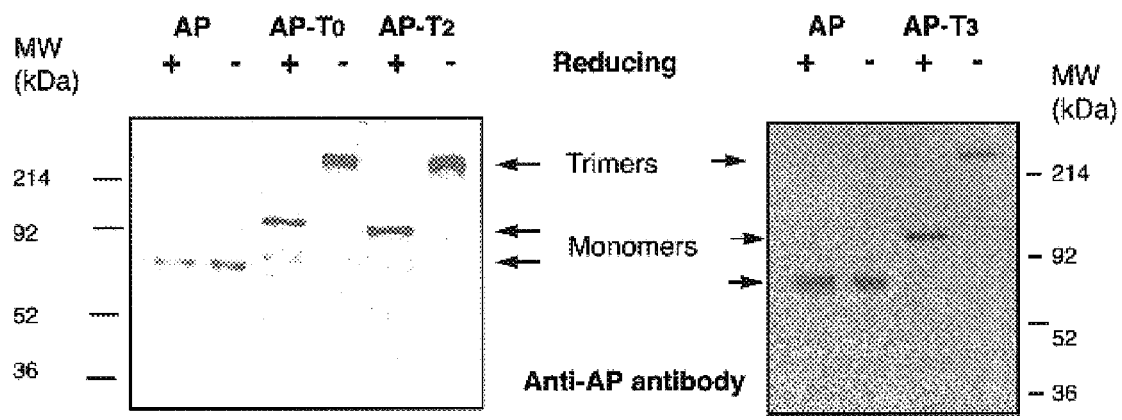
Figure 3:
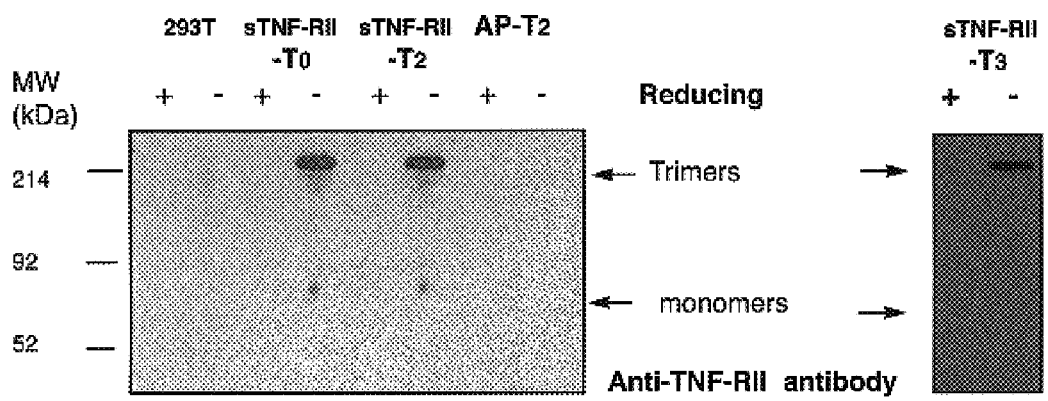
Figure 3:
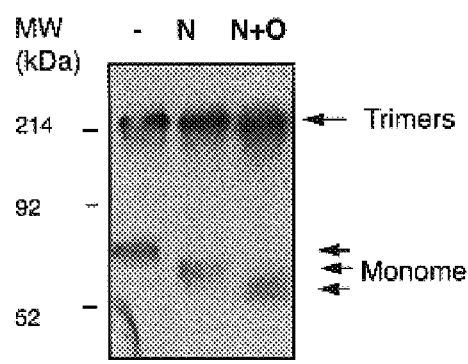
Figure 3:
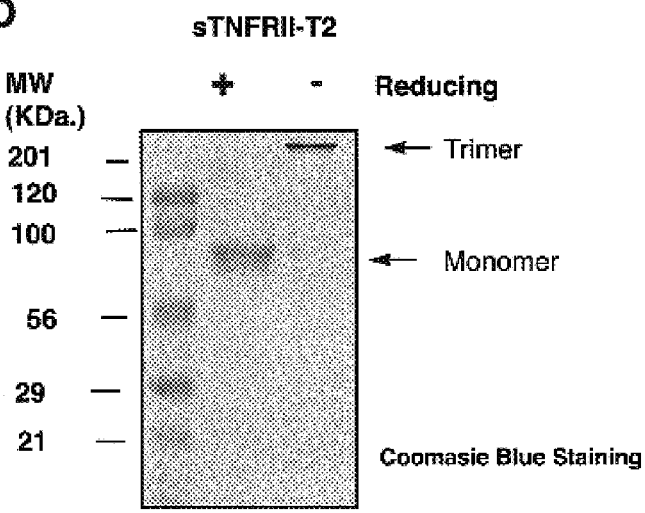

FIG. 3A. Western blot analysis of the trimerization of human placental alkaline phosphatase (AP) when fused to the C-propeptides of α(I) and α(III) collagens. The expression vectors encoding either AP alone or AP-C-propeptide fusions in pTRIMER vectors were transiently transfected into HEK293T cells. Forty-eight hours later, the conditioned media (20 μL) of each transfected cells as indicated were boiled for 5 minutes in equal volume of 2×SDS sample buffer either with or without reducing agent (mercaptoethanol), separated on a 10% SDS-PAGE and analyzed by Western blot using a polyclonal antibody to AP (GenHunter Corporation). Note the secreted 67 kDa AP alone does not form intermolecular disulfide bonds, whereas the secreted AP-T0 and AP-T2 fusions both are assembled efficiently into disulfide bond linked trimers (FIG. 3A, left panel). Similar result with efficient protein trimerization was also obtained when AP was fused to the C-propeptide of human α1(III) collagen (AP-T3) with a mutated putative BMP site (FIG. 3A, right panel).

FIG. 3B. Western blot analysis of the trimerization of soluble human TNF-RII when fused to the C-propeptides of α(I) and α(III) collagens. The expression vectors encoding either the AP-C-propeptide fusion (T2) (as a negative control for antibody specificity), or human soluble TNF-RII-C-propeptide fusions as indicated in pTRIMER vectors were transiently transfected into HEK293T cells. Conditioned media from HEK293T and HEK293T expressing AP-T2 were used as negative controls for TNFRII antibody specificity. Forty-eight hours later, the conditioned media (20 μL) of each non-transfected and transfected cells as indicated were boiled for 5 minutes in equal volume of 2×SDS sample buffer either with or without reducing agent (mercaptoethanol), separated on a 10% SDS-PAGE and analyzed by Western blot using a monoclonal antibody to human TNF-RII (clone 226, R & D Systems, Inc.). Note the monoclonal antibody can only recognize the secreted TNF-RII with disulfide bonds. Soluble TNF-RII-T0, TNF-RII-T2 and TNF-RII-T3 fusions are all assembled efficiently into disulfide bond linked trimers.

FIG. 3C. Trimerized sTNFRII is glycosylated. Two μL of sTNFRII-T2 from serum-free conditioned medium was digested under denaturing condition with either endoglycanase F (PNGase F which digests N-linked oligosaccharides) or PNGase F plus endo-o-glycosidase which recognizes serine/threonine linked (O-linked) oligosaccharides. The sTNFRII-T2 with and without deglycosylation was analyzed by Western blot using monoclonal antibody against TRFRII.

FIG. 3D. Purification of trimeric soluble TNFRII receptor. Soluble TNFRII-T2 was purified to homogeneity from serum-free conditioned medium of 293T cells stably expressing the fusion protein. Two μg of purified protein was analyzed under either reducing (with β-mercaptoethanol) or non-reducing conditions by a 10% SDS-PAGE and stained with Coomasie Blue. Note, as shown by western blot analysis shown in FIG. 3B, the purified soluble TNFRII-T2 fusion protein existed essentially in disulfide bond-linked trimeric form under non-reducing condition.

Figure 4:
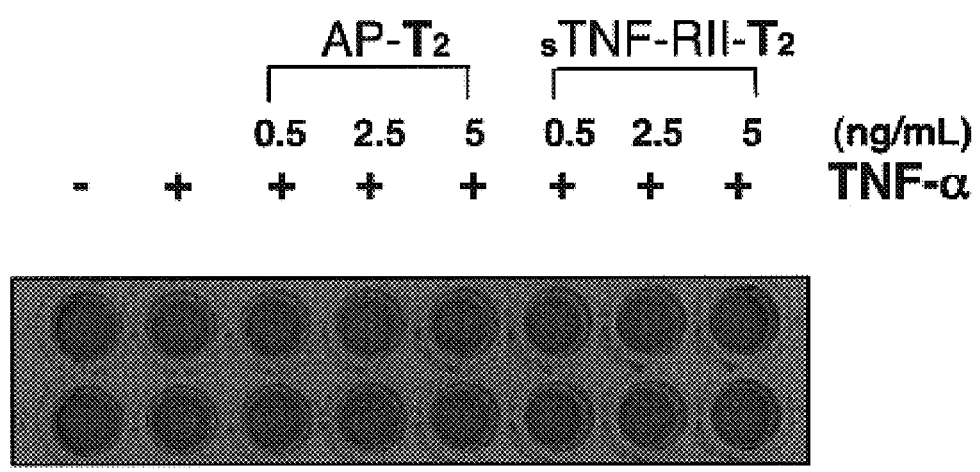
Figure 5:
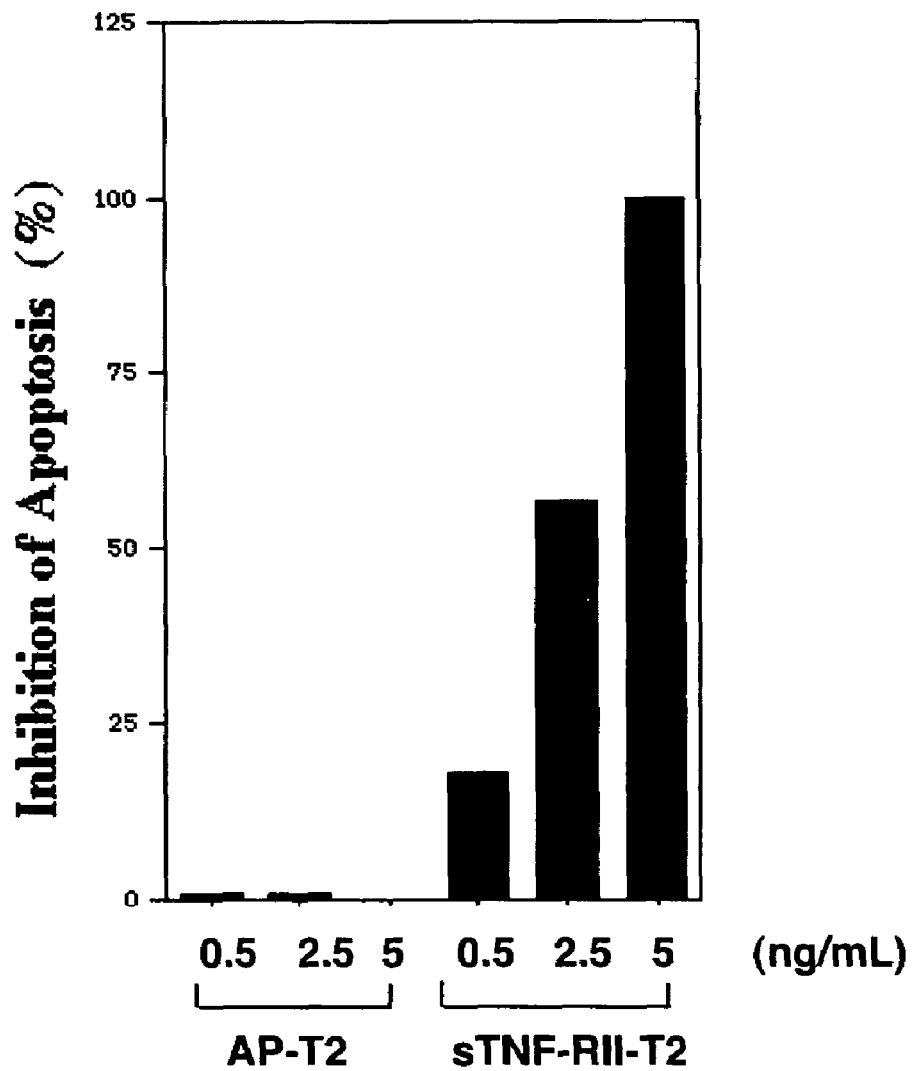

FIG. 4 and FIG. 5. illustrate the bioassays showing the potent neutralizing activity of the trimeric soluble human TNF-RII-C-propeptide fusion protein against human TNF-α mediated apoptosis.

FIG. 4. The TNF-α sensitive WEHI-13VAR cells (ATCC) were resuspended at 1 million cells/mL in RPMI medium containing 10% FBS. 100 μL of the cell suspension was plated into each well in a 96-well microtiter plate. Actinomycin D was added to each well at 500 ng/mL concentration followed by human TNF-α at 500 pg/ml (R & D Systems) in the presence or absence of trimeric soluble human TNF-RII-T2 as indicated. As a negative control, the trimeric AP-T2 was added in place of TNF-RII-T2. After 16 hours of incubation in a tissue culture incubator, the viability of cells was examined using either an inverted microscope at 20× magnification or cell viability indicator dye, Alamar Blue (BioSource, Inc.) added to 10% (v/v) to each well. The live cells are able to turn the dye color from blue to pink. Note that the trimeric soluble human TNF-RII-T2 exhibits a potent neutralizing activity against TNF-α the cells from TNF-α mediated apoptosis.

FIG. 5. Quantitative analysis of the neutralizing activity of trimeric soluble human TNF-RII-T2 against human TNF-α. The experiment was carried out as in FIG. 4. Two hours after adding the Alamar Blue dye, the culture medium as indicted from each well was analyzed at OD575. The readings were normalized against wells with either no TNF-α (100% viability) added or with TNF-α without neutralizing agent (0% viability) added.

Figure 6:
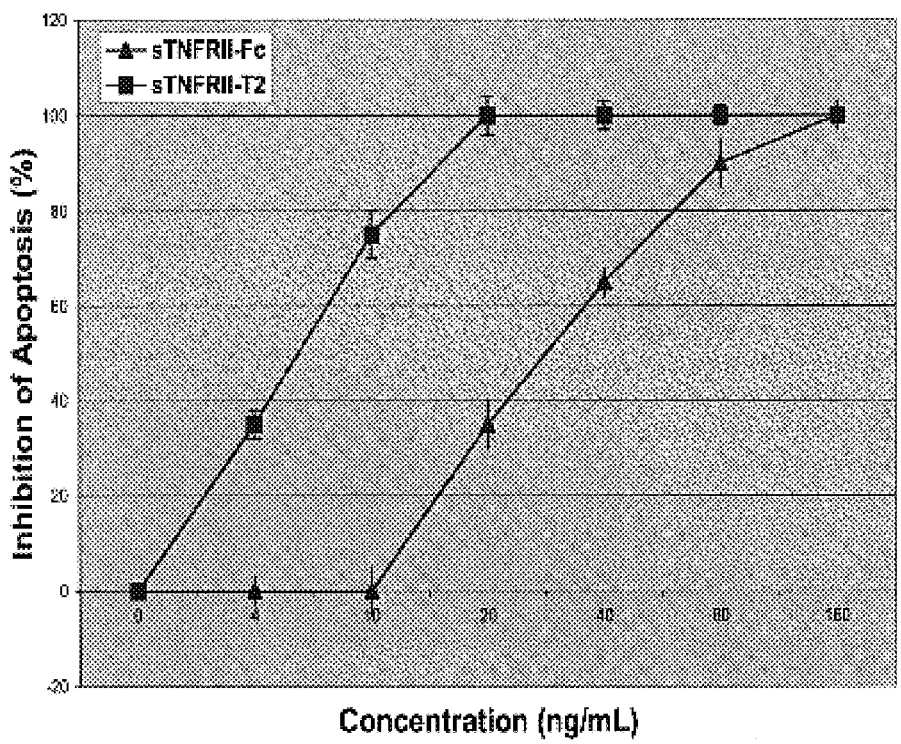
Figure 6:
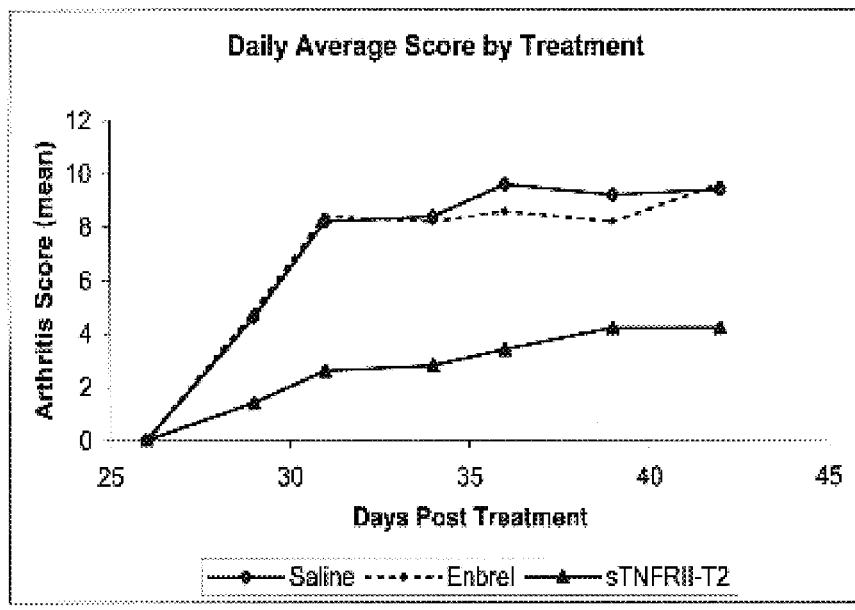

FIGS. 6A and 6B. Comparison of Biological activities of trimeric soluble human TNF-RII-Trimer fusion protein with dimeric soluble human TNF-RII-Fc fusion protein in neutralizing TNF-α and against collagen induced arthritis in mice FIG. 6A. Inhibition of TNF-α mediated apoptosis. TNF-α sensitive WEHI-13VAR cells were cultured in a 96-well microtiter plate in the absence or presence of either trimeric sTNFRII-T2 or dimeric sTNFRII-Fc to assess their ability to protect the cells from TNF-α mediated apoptosis. The experimental conditions were carried out as that in FIG. 4. The percentage of the TNF blockers in inhibition of TNF-mediated apoptosis was normalized against wells where either no TNF-α (100% viability), or with TNF-α without neutralizing TNF blockers (0% viability) added.

FIG. 6B. Comparison of trimeric soluble human sTNFRII-T2 fusion protein and dimeric sTNFRII-Fc (Enbrel®) in inhibiting collagen-induced arthritis (CIA) in DBA/1 mice as measured by arthritis scores (mean). The results were representative of 3 independent experiments.

DESCRIPTION OF SEQUENCE LISTINGS

SEQ ID NO: 1 (963 bases)
Nucleotide sequence encoding the C-propeptide human collagen α(I) T0 construct. The cDNA construct was cloned into the pAPtag2 vector, replacing the AP coding region.

SEQ ID NO:2 (311 aa)
The predicted C-propeptide T0 protein sequence of human Collagen α(I). The stretch of glycine repeats are located at the N-terminus.

SEQ ID NO:3 (771 bases)
Nucleotide sequence encoding the C-propeptide of human collagen α(I) T2 construct. The cDNA construct was cloned into pAPtag2 vector, replacing the AP coding region.

SEQ ID NO:4 (247 aa)
The predicted C-propeptide T2 protein sequence of human Collagen α(I). The mutated BMP-1 protease recognition site was located at the N-terminus.

(SEQ ID NO:5 (2487 bases)
Nucleotide sequence encoding the human placental alkaline (AP) fused to the T0 C-propeptide of human α(I) collagen (AP-T0).

SEQ ID NO:6(819aa)
The predicted protein sequence of the AP-T0 fusion protein.

SEQ ID NO:7 (2294 bases)
Nucleotide sequence encoding the human placental alkaline phosphatase (AP) fused to the T2 C-propeptide human α(I) collagen (AP-T2).

SEQ ID NO:8 (755 aa)
The predicted protein sequence of the AP-T2 Fusion.

SEQ ID NO:9 (1734 bases)
Nucleotide sequence encoding the human soluble TNF-RII fused to the T0 C-propeptide of human α(I) collagen (sTNF-RII-T0).

SEQ ID NO:10 (566 aa)
The predicted protein sequence of the human soluble TNF-RII-T0 Fusion.

SEQ ID NO: 11 (1542 bases)
Nucleotide sequence encoding the human soluble TNF-RII fused to the T2 C-propeptide of human α(I) collagen (sTNF-RII-T2).

SEQ ID NO:12 (502 aa)
The predicted protein sequence of the human soluble TNF-RII-T2 fusion protein.

SEQ ID NO:13 (2139 bases)
Nucleotide sequence encoding the human soluble CD4 fused to the T0 C-propeptide of human α(I) collagen.

SEQ ID NO:14 (699 aa)
The predicted Protein Sequence of the human soluble CD4-T0 Fusion. The amino acid residues in blue indicate fusion sites between human soluble CD4 and α(I) collagen T0 polypeptide.

SEQ ID NO:15 (1947 bases)
Nucleotide sequence encoding the human soluble CD4 fused to the T2 C-propeptide of human α(I) collagen.

SEQ ID NO:16 (635 aa)
The predicted Protein Sequence of the human soluble CD4-T2 Fusion. The amino acid residues in blue indicate fusion sites between human soluble CD4 and α(I) collagen T2 polypeptide.

SEQ ID NO: 17 (754 bases)
Nucleotide sequence encoding the C-propeptide of human collagen α1(III) T3 construct with mutated BMP-1 recognition site. The cDNA construct was cloned into pAPtag2 vector at BglII-XbaI sites, replacing the AP coding region. The flanking sequences denote restriction enzyme sites used in constructing the corresponding pTRIMER-T3 vector.

SEQ ID NO: 18 (246 aa)
The predicted C-propeptide T3 protein sequence of human Collagen α(III) with mutated BMP-1 recognition site located at the N-terminus.

SEQ ID NO: 19 (1536 bases)
Nucleotide sequence encoding the human soluble TNF-RII fused to the C-propeptide of human collagen α1(III) T3 construct with mutated BMP-1 recognition site.

SEQ ID NO: 20 (501 aa)
The predicted protein sequence of the human soluble TNF-RII fused to human collagen α1(III) T3 construct with mutated BMP-1 recognition site.

DESCRIPTION OF THE INVENTION

Prior to setting forth the invention, it may be helpful to an understanding thereof to set forth definitions of certain terms to be used hereinafter.

DNA Construct: A DNA molecule, generally in the form of a plasmid or viral vector, either single- or double-stranded that has been modified through recombinant DNA technology to contain segments of DNA joined in a manner that as a whole would not otherwise exist in nature. DNA constructs contain the information necessary to direct the expression and/or secretion of the encoding protein of interest.

Signal Peptide Sequence: A stretch of amino acid sequence that acts to direct the secretion of a mature polypeptide or protein from a cell. Signal peptides are characterized by a core of hydrophobic amino acids and are typically found at the amino termini of newly synthesized proteins to be secreted or anchored on the cell surface. The signal peptide is often cleaved from the mature protein during secretion. Such signal peptides contain processing sites that allow cleavage of the signal peptides from the mature proteins as it passes through the protein secretory pathway. A signal peptide sequence when linked to the amino terminus of another protein without a signal peptide can direct the secretion of the fused protein. Most of the secreted proteins, such as growth factors, peptide hormones, cytokines and membrane proteins, such as cell surface receptors, contain a signal peptide sequence when synthesized as a nascent protein.

Soluble receptor: The extracellular domain, in part or as a whole, of a cell surface receptor, which is capable of binding its ligand. Generally, it does not contain any internal stretch of hydrophobic amino acid sequence responsible for membrane anchoring.

C-propeptide of collagens: The C-terminal globular, and non-triple-helical domain of collagens, which is capable of self-assembly into trimers. In contrast to the triple helical region of collagens, the C-propeptide does not contain any glycine repeat sequence and is normally proteolytically removed from procollagen precursor upon procollagen secretion before collagen fibril formation.

Glycine repeats: The central linear triple helix forming region of collagen which contains hundreds of $(Gly-X-Y)_n$ repeats in amino acid sequence. These repeats are also rich in proline at X or/and Y positions. Upon the removal of N-and C-propeptides, the glycine-repeats containing collagen triple helices can assemble into higher order of insoluble collagen fibrils, which make up the main component of the cell matrix.

cDNA: Stands for complementary DNA or DNA sequence complementary to messenger RNA. In general cDNA sequences do not contain any intron (non-protein coding) sequences.

One of the modern strategies for treating autoimmune diseases involves the use of biologic TNF antagonists, such as soluble receptors or therapeutic antibodies. However, current TNF-α biologic blockers are all dimeric in structure, whereas TNF-α itself is homotrimeric in nature. Here we describe a general methodology for efficient creation of trimeric soluble receptors. The process involves gene fusion between a soluble receptor with a ligand binding domain and a trimerization tag from the C-propeptide domain of pro-collagen (TRIMER tag), which is capable of self-assembly into a covalently linked trimer. Using both in vitro bioassays and an in vivo mouse model for collagen-induced arthritis (CIA), we show that the homotrimeric soluble TNF receptor produced with such method is a more potent blocker than dimeric TNF receptor decoys in inhibiting TNF-α signaling. Thus, TRIMER tag provides a new platform for rational design of the next generation biologic drugs against autoimmune diseases.

Prior to this invention, nearly all therapeutic antibodies and soluble receptor-Fc fusion proteins, such as Enbrel®, are dimeric in structure (FIGS. 1A-1D). Although these molecules, compared to their monomeric counterparts, have been shown to bind their target antigens or ligands with increased avidity, it is predicted that they are still imperfect, due to structural constrains, to bind their targets that have a homotrimeric structure. Examples of such therapeutically important trimeric ligands include TNF family of cytokines and HIV coat protein gp120. Therefore, from a structural point of view, it will be desirable to be also able to generate trimeric soluble receptors or antibodies, which can perfectly dock to their target trimeric ligands or antigens (FIGS. 1A-ID), and thereby completely block the ligand actions. Such trimeric soluble receptors or chimeric antibodies are expected to have the highest affinity to their targets and thus can be used more effectively and efficiently to treat diseases such as arthritis and AIDS.

This invention discloses ways for generating such secreted trimeric receptors and biological active proteins by fusing them to the C-propeptides of collagen, which are capable of self-assembly into trimers. The following are the advantages of this invention: (1) collagen is the most abundant protein secreted in the body of a mammal, constituting nearly 25% of the total protein in the body; (2) the major forms of collagen naturally occur as trimeric helixes, with their globular C-propeptides responsible for the initiating of trimerization, which are subsequently proteolytically cleaved upon triple helix formation; (3) the cleaved soluble trimeric C-propeptide of collagen is found naturally at sub microgram/mL level in the blood of mammals; (4) the linear triple helical region of collagen can be included as a linker or excluded as part of the fusion protein so the distance between a protein to be trimerized and the C-propeptide of collagen can be precisely adjusted to achieve an optimal biological activity; (5) the recognition site of BMP1 which cleaves the C-propeptide off the pro-collagen can be mutated or deleted to prevent the disruption of a trimeric fusion protein; (6) the C-propeptides domain provides a universal affinity tag, which can be used for purification of any secreted fusion proteins created by this invention; (7) unlike the IgG1 Fc tag which is known to be have other biological functions such as binding to its own cell surface receptors, the only known biological function of the C-propeptide of collagen is its ability to initiate trimerization of nascent pro-collagen chains and keep the newly made pro-collagen trimer soluble before assembly into insoluble cell matrix. These unique properties of the C-propeptide of collagen would predict that this unique trimerization tag is unlikely going to be toxic, or immunogenic, making it an ideal candidate for therapeutic applications.

To demonstrate the feasibility for making secreted trimeric fusion proteins, cDNA sequences encoding the entire C-propeptides of human α1(I) collagen containing either 11 glycine-repeats from the triple helical region (T0 construct, SEQ ID NOS:1-2), or no glycine-repeat with BMP-1 recognition site (-RADD-) mutated to abolish proteolytic cleavage of the TRIMER tag (T2 construct, SEQ ID NO:3-4) were amplified by PCR using EST clones purchased from the American Type Culture Collection (ATCC). The amplified cDNAs were each cloned as a Bgl II-XbaI fragment into the pAPtag2 mammalian expression vector (GenHunter Corporation; Leder et al., 1996 and 1998), replacing the AP coding region (FIGS. 2A and 2B). The resulting vectors are called pTRIMER, versions T0 and T2, respectively. Using the same approach, the entire C-prodomain of human α1 (III) collagen with a mutated BMP-1 recognition site and without any glycine-repeats (T3 construct, SEQ ID No: 17-18) was also amplified by PCR and cloned into pAPtag2 mammalian expression vector. The resulting vector is designated pTrimer-T3. These vectors allow convenient in-frame fusion of any cDNA template encoding a soluble receptor or biologically active protein at the unique Hind III and Bgl II sites. Such fusion proteins have the collagen trimerization tags located at the C termini, similar to native pro-collagens.

For trimeric AP and soluble TNFRII protein fusion constructs, the entire AP coding region and cDNA encoding the soluble TNFRII (aa 1-256) without the trans-membrane and cytoplasmic domain were amplified by PCR and cloned into either Hind III or Bgl II sites of pTRIMER expression vectors to allow in-frame fusion with the TRIMER tags of the C-propeptide. All fusion constructs were verified by DNA sequence analysis using an ABI 3100 DNA sequencer.

EXAMPLE 1

To demonstrate the feasibility of this invention, a cDNA encoding the human secreted placental alkaline phosphatase (AP), including its native signal peptide sequence, was cut out as a Hind III-Bgl II fragment from the pAPtag4 vector (GenHunter Corporation; Leder et al., 1996 and 1998) and cloned into the corresponding sites of the pTRIMER-T0, pTRIMER-T2 and pTRIMER-T3 vectors. The resulting AP-collagen fusion constructs (SEQ ID NOS:5-8) were expressed in HEK293T cells (GenHunter Corporation) after transfection. The successful secretion of the AP-collagen fusion proteins can be readily determined by AP activity assay using the conditioned media of the transfected cells. The AP activity reached about 1 unit/mL (or equivalent to about 1 μg/mL of the fusion protein) 2 days following the transfection. To obtain HEK293T cells stably expressing the fusion proteins, stable clones were selected following co-transfection with a puromycine-resistant vector, pBabe-Puro (GenHunter Corporation). Clones expressing AP activity were expanded and saved for long-term production of the fusion proteins.

To determine if the AP-collagen fusion proteins are assembled into disulfide bond-linked trimers, conditioned media containing either AP alone or AP-T0, AP-T2 and AP-T3 fusions were boiled in SDS sample buffers containing either without (non-reducing) or with β-mercaptoethanol (reducing), separated by an SDS PAGE and analyzed by Western blot using an anti-AP polycloning antibody (GenHunter Corporation). AP alone without fusion exhibited as a 67 kDa band under both non-reducing and reducing conditions, consistent with the lack of any inter-molecular disulfide bonds as expected (FIG. 3A). In contrast, AP-T0, AP-T2 and AP-T3 fusion proteins secreted were shown to be three times as big (about 300 kDa) under the non-reducing condition as those under the reducing condition (90-100 kDa), indicating that both fusion proteins were assembled completely into homotrimers (FIG. 3A). This result essentially reduces the concept of this invention to practice.

EXAMPLE 2

To provide a proof that new and therapeutically beneficial biological functions can be endowed to a trimeric fusion protein, we next constructed a trimeric human soluble TNF-RII (p75) receptor using a corresponding EST clone purchased from the ATCC. As described in Example 1, the N-terminal region of human TNF-RII, including the signal peptide and the entire ligand-binding region, but excluding the transmembrane domain, was cloned in-frame, as a Bam H I fragment, into the Bgl II site of pTRIMER-T0, pTRIMER-T2 and pTRIMER-T3 vectors. The resulting fusion constructs were expressed in either HEK293T or CHO cells following transfection. Stable clones were obtained by puromycine co-selection as described in Example 1. Western blot analysis under both non-reducing and reducing conditions was carried out to determine if the resulting soluble TNF-RII-collagen fusion proteins were indeed expressed, secreted and assembled into trimeric forms. As expected, the monoclonal antibody against human TNF-RII (clone 226 from R & D Systems, Inc.) clearly recognized the trimeric soluble TNF-fusion proteins expressed by all three (T0, T2 and T3) fusion vectors as 220-240 kDa bands, which are about three times bigger than the corresponding monomeric fusion proteins (FIG. 3B). The TNF-RII antibody failed to detect monomeric fusion proteins under reducing conditions, consistent with the property specified by the antibody manufacturer. As a negative control for antibody specificity, neither the HEK293T cell alone, nor the cells expressing AP-T2 fusion protein expressed any TNF-RII (FIG. 3B). To determine whether trimerized soluble TNFRII was properly glycosylated, sTNFRII-T2 from serum-free conditioned medium was digested with endoglycanase F (PNGase F which digests N-linked oligosaccharides) and PNGase F plus endo-o-glycosidase which recognizes serine/threonine linked (O-linked) oligosaccharides. The result shown in FIG. 3C clearly indicated that the recombinant protein was heavily glycosylated with both N- and O-linked oligosaccharides, which is evident by the more visible shift in molecularweight of the minor monomeric form of sTNFRII-T2 that appeared to be preferentially detected by the western blot (FIG. 3C). To obtain the sTNFRII-TRIMER in purified form for functional analysis, sTNFRII-T from serum-free conditioned medium was purified to homogeneity essentially following a previously described procedure for the purification of the C-propeptide of Type I collagen (Bernocco et al.). As expected, the purified sTNFRII-T2 detected by Coomassie blue staining existed mostly in covalently linked trimeric form under non-reducing condition (FIG. 3D).

Expression vectors were either transiently or stably transfected into either HEK293T (GenHunter Corp.) or CHO cells (ATTC) using FuGENE 6 (Roche). The expression vectors encoding either AP-TRIMER or sTNFRII-TRIMER fusion proteins in pTRIMER vectors were transiently transfected into HEK293T cells. 48 hours later, the conditioned media (20 µL) of each transfected cells as indicated were boiled for 5 min in equal volume of 2×SDS sample buffer either without or with reducing agent (mercaptoethanol), separated on a 10% SDS-PAGE and analyzed by Western blot. Secretion of trimeric AP was monitored by both AP activity assay using AP assay A (GenHunter Corp.) and Western blot analysis using polyclonal antibody against human placenta AP (GenHunter Corp.). Trimeric soluble TNFRII receptors were analyzed by Western blot using monoclonal antibody clone 226 (R & D System) under non-reducing condition. Deglycosylation of asparagine-linked (N-linked) and serine/threonine-linked (O-linked) carbohydrates from sTNFRII-T2 in serum free conditioned medium was completed with endoglycanase F (PNGaseF) and endo-o-glycosidase (Prozyme), respectively, following the protocol recommended by the manufacturer. For purification of trimeric soluble TNFRII, 293T cells stably expressing the fusion proteins were cultured first in DMEM with 10% BCS and 1% Pennstrep until confluence. The cells were then switched to HyQ PF293 serum-free medium (Hyclone) after washing 5 times with PBS. After 5-7 days, the conditioned media was used as a starting material for purification. The trimeric fusion protein from 200 mL of conditioned medium was purified to homogeneity using method essentially as described previously for C-propeptide of collagen (Chen, Y., et al.). Purified TNFRII-T2 from the last purification step (Butyl-Sepharose) was dialyzed in PBS before used for biological assays.

To determine if the trimeric soluble TNF-RII receptors are potent inhibitors of its trimeric ligand TNF-α, TNF-α bioassay was carried out using a cytokine sensitive cell line WEHI-13VAR (ATCC) essentially as described previously (Mohler et al., 1993).

TNF-α bioassays were carried out in duplicate for each data point in a 96-well plate using a cytokine sensitive cell line WEHI-13VAR (ATCC) essentially as described previously (Mohler et al. and Khabar et al.). Briefly, exponentially growing WEHI-13VAR cells were resuspended at 1 million cells/mL in RPMI medium containing 10% FBS (Hyclone). 100 µL of the cell suspension was plated into each well in a 96-well microtiter plate. Actinomycin D was added to each well at 500 ng/mL concentration followed by human TNF-α at 250 pg/ml (R & D Systems) in the presence or absence of either sTNFRII-Fc (R & D systems, or Amgen) and trimeric soluble human sTNF-RII-T2 as indicated. Both purified sTNFRII-T2 and sTNFRII-Fc were serially diluted in PBS with 1 mg/mL of BSA before used. After 16 hours of incubation in a tissue culture incubator, the viability of cells was examined using either an inverted microscope at 20× magnification or cell viability indicator dye, Alamar Blue (BioSource) added to 10% (v/v) to each well. The live cells are able to turn the dye color from blue to pink, which can be quantified at OD575. Percentage in inhibition of apoptosis was normalized against 0% and 100% inhibition without and with TNF-α added only, respectively. Each data points were measured from experimental duplicates.

The result shown in FIGS. 4 and 5 clearly indicated that the trimeric soluble TNF-RII-C-propeptide fusion proteins are extremely potent in neutralizing the TNF-α mediated apoptosis of WEHI-13VAR cells in the presence of Actinomycin D (500 ng/mL) (Sigma). When human TNF-α (R & D Systems) was used at 0.5 ng/mL, the trimeric soluble TNF-RII-T2 (both from serum-free media or in purified form) had an apparent Ki-50 (50% inhibition) of about 2 ng/mL or $8 \times 10^{-12}$ M (assuming the MW of 240 kDa as homotrimer). This affinity to TNF-α is 4 orders of magnitude higher than that of the monomeric TNF-RII and about 5-10 times higher than that of the dimeric soluble TNF-RII-Fc fusion, such as Enbrel® (Mohler et al., 1993) in a side by side comparison (FIG. 6A). Similar results in blocking TNF activity were also obtained for sTNF-RII-T0 and sTNF-RII-T3 fusion proteins.

This crucial example proves that this invention can create trimeric fusion proteins with new biological properties that may have great therapeutic applications. Such soluble trimeric human TNF receptors may prove to be much more effective than the current dimeric soluble TNF receptor (e.g. Enbrel®) on the market in treating autoimmune diseases such as RA. The dramatically increased potency of trimeric-TNF receptors could greatly reduce the amount of TNF blockers to be injected weekly for each patient, while improving the treatment and significantly lowering the cost for the patients. The improved potency of trimeric TNF receptors should also alleviate the current bottleneck in dimeric TNF receptor production, which currently can only meet the demands in treating about 100,000 patients in the United States.

EXAMPLE 3

To test the biological activity of the trimeric soluble TNFR in vivo, we then used the mouse model for collagen-induced arthritis (CIA) (Chen, Y., et al.). For mouse CIA model, the standard protocol with two immunization regimens was followed (Chen, Y., et al.). Briefly, 6-8 weeks old male DBA/1 mice were purchased from Jackson laboratory and immunized intradermally each at the base of tail with 100 µg of bovine Type II collagen (Condrex) in complete Freund's adjuvant (CFA) (Condrex). The mice were boosted after 3 weeks with 100 µg of bovine Type II collagen in incomplete Freund's adjuvant (IFA) (Condrex) to initiate the CIA. At the same time of boost injections, mice were randomly divided into 4 treatment groups of 5-6 animals. Each group received either 100 µl of vehicle (PBS), 20 µg of purified trimeric sTNFRII-T2 in 100 µl PBS, 20 µg of purified trimeric sTN-FRII-T2 in 100 µl PBS, or 20 µg of sTNFRII-Fc (Enbrel®) (Amgen, Lot Number: P055643) in 100 µl PBS, respectively, all via i.p. injections. Mice were monitored daily over a 6 weeks period from the initial immunization for signs of arthritis. Standard scoring system for arthritis index was followed with 0=no swelling, 1=paw swelling with single digit, 2=paw swelling with multiple digits and 3=severe paw swelling and joint rigidity. Each limb was graded, giving a maximum possible score of 12 per mice. Statistical analysis of daily average arthritis scores was conducted using F test statistics based on Wilks' Lambda, and their p-values for multivariate procedures, as recommended by LaTour and Miniard (LaTour and Miniard, 1983).

In a side-by-side comparison with the dimeric sTNFRII-Fc fusion protein (Enbrel®) from Amgen®, the trimeric sTN-FRII-T2 fusion protein exhibited significant more potent effect, with over 50% inhibition of the arthritis manifestation at any given day post treatment based on mean arthritis scores (P<0.0435), than Enbrel® which gave little protection as compared with the negative Saline control (FIG. 6B). The minimum effect observed for Enbrel® could be due to the lower dose (20 µg/mouse) used here than that of previously published (50 µg/mouse) (Wooley et al.). The lower dose was chosen to best demonstrate the superiority, if any, of the trimeric sTNFRII fusion proteins. If one considers the in vitro potency for both the dimeric and trimeric sTNFRII (in the range of ng/ml) in blocking TNF-α, and that each mouse contains no more than 2-3 ml of blood, 20 µg/mouse would translate to microgram/mL level of either type of TNF blockers if they are completely absorbed into the circulation. This is about 3 orders of magnitude higher concentration than their Kis. Obviously, incomplete absorption into the circulation and rapid turnover (degradation) could significantly affect the final effective serum concentration of these fusion proteins. Compared to previously published CIA studies conducted with either dimeric soluble TNFRII-Fc fusion protein (Wooley et al.) or anti-TNF antibodies (Williams et al.), the trimeric soluble TNFRII also exhibited significantly better effect in suppressing disease severity even when used at a lower dose.

Taken together, we have demonstrated that with the TRI-MER tags from pro-collagens, any soluble receptors or secreted proteins can be efficiently trimerized and expressed as secreted proteins. Such trimeric fusion proteins are trivalent in structure with a 3-fold symmetry and thus may have superior biological properties than that of either naturally occurring or existing biologic proteins. Such soluble trimeric human TNF receptors may prove to be more effective than the current dimeric soluble TNF receptor (e.g. Enbrel®) or therapeutic antibodies on the market in treating autoimmune diseases such as RA. The increased potency of trimeric-TNF receptors has the potential to significantly reduce the amount of TNF blockers to be injected weekly for each patient, while improving the treatment and significantly lowering the cost for the patients. Obviously, such clinical benefits will also depend on if a trimeric TNFR soluble receptor has superior pharmacokinetics properties, such as high stability and low toxicity in the human body. Future clinical trials should provide such pivotal information.

The advantages of using C-propeptide of collagen as a trimerization tag are: (1) collagen is the most abundant protein secreted in the body of a mammal, consisting of 25% of total proteins, and the trimeric C-propeptide of pro-collagen proteolytically released from the mature collagen is found naturally in the blood of mammals and is not known to be toxic to the body; (2) the recognition site of BMP1 which cleaves the C-propeptide off the pro-collagen can be mutated or deleted to prevent the disruption of a trimeric fusion protein; (3) the C-propeptide domain provides a universal affinity tag, which can be used for purification of any secreted fusion proteins created with the method; (4) unlike the Fc receptor, there is no known receptor for the C-propeptides that could lead to off-target or undesired side effects. Given the fact that a homotrimer is trivalent and has a 3-fold symmetry, whereas a homodimer is bivalent and has only a 2-fold symmetry, the two distinct structural forms theoretically can never be perfectly overlaid (FIGS. 1A-1D). As such, neither the homodimeric soluble TNFR-Fc (e.g. Enbrel®), nor TNF-α antibodies could have had an optimal interface for binding to their corresponding homotrimeric ligands, TNF-α. In contrast, homotrimeric soluble TNF receptors created by the TRIMER tag method described here have the potential structurally to perfectly dock to the corresponding homotrimeric ligands. Thus, these trimeric soluble receptor analogs could be more effective in neutralizing the biological activities of their trimeric ligands, as has been demonstrated here for TNF-α. Conceivably, chimeric antibodies in trimeric form can also be created with the TRIMER tag method, which may significantly increased the avidity in neutralizing their trimeric antigens.

It should be pointed out that, unlike Fc tag which binds to protein A tightly, purification of trimerized proteins fused to C-propeptide of collagen may be more difficult than Fc fusion proteins. Although it is generally believed that TNF family of ligands are mostly homotrimeric in solution or based on x-ray crystallography, biological functional assays and structural analysis of recombinant TNF expressed in bacteria suggested that both trimeric and dimeric forms of the ligand could co-exist (Schoenfeld et al.).

EXAMPLE 4

The HIV virus, the cause of AIDS, infects and destructs primarily a special lineage of T lymphocytes in our body. These so called CD4+ T cells express a cell surface protein dubbed CD4, which is the receptor of HIV. HIV recognizes the CD4+ cells with its viral coat protein gp120 that binds to CD4. Notably, the gp120 exists as a giant homotrimeric complex on the viral surface, whereas the CD4 is monomeric on the cell surface. The current model for HIV infection is that of a complete docking of HIV to CD4+ T cells, when all three subunits of gp120 trimers are each bound to CD4 is required for viral RNA entry into the cells. Obviously, one of the straightforward strategies for stopping HIV infection is to use soluble CD4 to blind the virus. Indeed, such approach using both monomeric soluble CD4 and CD4-Fc fusions has been shown quite effective in curbing HIV infections of laboratory isolates (Clapham et al., 1989; Daar et al., 1990). Unfortunately, these soluble CD4 were less effective in stopping the infection of HIV viral strains found in AIDS patients (Daar et al., 1990), possibly due to the amino acid sequence variations of the gp120, which lowers the affinity to monomeric and dimeric soluble CD4s.

To significantly increase the affinity of a soluble CD4 to any gp120 variants on HIV viruses, ideally a soluble CD4 should be in trimeric form so it can perfectly dock to its trimeric ligand, gp120 homotrimers. One of the major challenges for combating AIDS has been the high mutational rate of the viral genome, which leads to drug resistance. Therefore any drugs that directly target viral genes, such as HIV reverse transcriptase (e.g. AZT) and protease, are likely rendered ineffective as a result of viral mutations. In contrast, no matter how much it mutates, a HIV virus has to bind to a cellular CD4 receptor to initiate the infection. Thus, a high affinity soluble CD4 trimer should be immune to viral mutations because viral mutations in gp120 genes will render the virus unable to bind not only to a trimeric soluble CD4, but also CD4 on the cells.

To create such trimeric soluble CD4 HIV receptor analogs, a cDNA encoding the entire human soluble CD4, including its native signal peptide sequence, but excluding the transmembrane and the short cytoplasmic domains, was amplified using an EST clone purchased from the ATCC. The resulting cDNA was then cloned as a Hind III-Bgl II fragment into the corresponding sites of the pTRIMER-T0 and pTRIMER-T2 expression vectors. The resulting soluble CD4-collagen fusion constructs (SEQ ID NOS:13-16) were expressed in HEK293T cells (GenHunter Corporation) after transfection. To obtain HEK293T cells stably expressing the fusion proteins, stable clones were selected following co-transfection with a puromycine-resistant vector, pBabe-Puro (GenHunter Corporation). Clones expressing the fusion proteins were expanded and saved for long-term production of the fusion proteins.

To determine if the soluble human CD4-collagen fusion proteins are assembled into disulfide bond-linked trimers, conditioned media containing soluble CD4-T0 and CD4-T2 fusions were boiled in SDS sample buffers containing either without (non-reducing) or with β-mercaptoethanol (reducing), separated by a SDS PAGE and analyzed by Western blot using an monoclonal antibody to human CD4 (R & D Systems). Both soluble CD4-T0 and CD4-T2 fusion proteins secreted were shown to be three times as big (about 300 kDa) under the non-reducing condition as those under the reducing condition (90-100 kDa), indicating they were assembled essentially completely into homotrimers (data not shown). Now these trimeric soluble CD4 can be readily tested for gp120 binding and anti-HIV infection.

REFERENCES

U.S. Patent Documents
U.S. Pat. No. 5,155,027, Issued October 1992, Sledziewski et al.
U.S. Pat. No. 5,605,690, Issued February 1997, Jacobs et al.
U.S. Pat. No. 5,843,725, Issued December 1998, Sledziewski et al.
U.S. Pat. No. 6,171,827, Issued January 2001, Bulleid et al.
U.S. Pat. No. 6,277,600, Issued August 2001, Tomita et al.
U.S. Pat. No. 5,554,499, Issued September 1996, Leder et al.
U.S. Pat. No. 5,801,000, Issued September 1998, Leder et al.
U.S. Pat. No. 6,897,039, Issued May 2005, Graversen et al.

Other References
Daar et al. Proc. Natl. Acad. Sci. 87:6574-6578 (1990)
Alvares et al. Biochemistry 38:5401-5411 (1999)
Kwong et al. Nature 393:648-659 (1998).
Clapham et al. British Medical Bulletin 58: 43-59 (2001).
Clapham et al. Nature 337:368-370 (1989).
Locksley, R. M., Killeen, N. & Lenardo, M. J. The TNF and TNF receptor superfamilies: integrating mammalian biology. Cell 104, 487-501 (2001).
Feldmann, M. & Maini, R. N. Anti-TNF alpha therapy of rheumatoid arthritis: what have we learned? Annu Rev Immunol. 19, 163-196 (2001).
Idriss, H. T. & Naismith, J. H. TNF alpha and the TNF receptor superfamily: structure-function relationship(s). Microsc Res Tech. 50, 184-195 (2000).
Mohler, K. M. et al. Soluble tumor necrosis factor (TNF) receptors are effective therapeutic agents in lethal endotoxemia and function simultaneously as both TNF carriers and TNF antagonists. J Immunol. 151, 1548-1561 (1993).
Feldmann, M. Development of anti-TNF therapy for rheumatoid arthritis. Nat Rev Immunol. 2, 364-371 (2002).
Yang, X., Farzan, M., Wyatt, R. & Sodroski, J. Characterization of stable, soluble trimers containing complete ectodomains of human immunodeficiency virus type 1 envelope glycoproteins. J. Virol. 74, 5716-5725 (2000).
Frank, S. et al. Stabilization of short collagen-like triple helices by protein engineering. J. Mol. Biol. 308, 1081-1089 (2001).
Chen, B. et al. A chimeric protein of simian immunodeficiency virus envelope glycoprotein gp140 and *Escherichia coli* aspartate transcarbamoylase. J. Virol. 78, 4508-4516 (2004).
Stryer, L. in "Connective-Tissue Proteins", Biochemistry, 3$^{rd}$ edition, pp261-281 (1989). W.H. Freeman and Company, New York.
Prockop, D. J., Sieron, A. L. & Li, S. W. Procollagen N-proteinase and procollagen C-proteinase. Two unusual metalloproteinases that are essential for procollagen processing probably have important roles in development and cell signaling. Matrix Biol. 16, 399-408 (1998).
Li, S. W., Sieron, A. L., Fertala, A., Hojima, Y., Arnold, W. V. & Prockop, D. J. The C-proteinase that processes procollagens to fibrillar collagens is identical to the protein previously identified as bone morphogenic protein-1. Proc Natl Acad Sci USA. 93, 5127-5130 (1996).
Melkko, J., Niemi, S., Risteli, L. & Risteli, J. Radioimmunoassay of the carboxyterminal propeptide of human type I procollagen. *Clinical Chemistry* 36, 1328-1332 (1990).
Sorva, A. et al. Familial high serum concentrations of the carboxyl-terminal propeptide of type I procollagen. Clin Chem. 40, 1591-1593 (1994).
Bernocco, S. et al. Biophysical characterization of the C-propeptide trimer from human procollagen III reveals a tri-lobed structure. J Biol Chem. 276, 48930-48936 (2001).
Khabar, K. S., Siddiqui, S. & Armstrong, J. A. WEHI-13VAR: a stable and sensitive variant of WEHI 164 clone 13 fibrosarcoma for tumor necrosis factor bioassay. Immunol Lett. 46, 107-110 (1995).
Chen, Y., Rosloniec, E., Price, J., Boothby, M. & Chen, J. Constitutive expression of BCL-X(L) in the T lineage attenuates collagen-induced arthritis in Bcl-X(L) transgenic mice. Arthritis Rheum. 46, 514-521 (2002).

Wooley, P. H., Dutcher, J., Widmer, M. B. & Gillis, S. Influence of a recombinant human soluble tumor necrosis factor receptor FC fusion protein on type II collagen-induced arthritis in mice. J Immunol. 151, 6602-6607 (1993).

Williams, R. O., Feldmann, M., Maini, R. N. Anti-tumor necrosis factor ameliorates joint disease in murine collagen-induced arthritis. Proc Natl Acad Sci USA. 89, 9784-9788 (1992).

Schoenfeld, H. J. et al. Efficient purification of recombinant human tumor necrosis factor beta from *Escherichia coli* yields biologically active protein with a trimeric structure that binds to both tumor necrosis factor receptors. J Biol Chem. 266, 3863-3869 (1991).

LaTour, S. & Miniard, P. W. The Misuse of Repeated Measures Analysis in Marketing Research, J. Marketing Res. 20, 45-57 (1983).

Yang, X., Farzan, M., Wyatt, R. & Sodroski, J. Characterization of stable, soluble trimers containing complete ectodomains of human immunodeficiency virus type 1 envelope glycoproteins. J. Virol. 74, 5716-5725 (2000).

Frank, S. et al. Stabilization of short collagen-like triple helices by protein engineering. J. Mol. Biol. 308, 1081-1089 (2001).

Holtet T. L. et al. Tetranectin, a trimeric plasminogen-binding C-type lectin. Protein Science 6, 1511-1515 (1997).

What is claimed is:

1. A method for reducing TNF-alpha activity in a mammal having a TNF-alpha-mediated disorder which comprises administering to said mammal a therapeutically effective amount of a disulfide bond-linked trimeric fusion protein comprising three fused protein subunits, wherein each fused protein subunit comprises a soluble TNF-alpha receptor or functional portion thereof containing a TNF binding domain, which in turn is fused to a C-terminal portion of collagen capable of self-trimerizing said fused protein subunit to form said disulfide bond-linked trimeric fusion protein containing three TNF ligand binding domains, wherein said trimeric fusion protein has a greater binding affinity to a TNF ligand as compared to a monomeric TNF ligand binding domain.

2. The method of claim 1, wherein the disulfide bond-linked trimeric fusion protein is administered by subcutaneous injection.

3. The method of claim 1, wherein the disulfide bond-linked trimeric fusion protein is administered by intravenous injection.

4. The method of claim 1, wherein the disulfide bond-linked trimeric fusion protein is administered in a series of doses separated by intervals of days or weeks.

5. The method of claim 1, wherein the TNF-alpha-mediated disorder is an arthritic condition.

6. The method of claim 1, wherein the TNF-alpha-mediated disorder is Crohn's disease.

7. The method of claim 1, wherein the TNF-alpha-mediated disorder is psoriasis.

8. The method of claim 1, wherein the TNF-alpha-mediated disorder is an inflammatory disorder.

9. The method of claim 1, wherein the TNF-alpha-mediated disorder is sepsis.

10. The method of claim 1, wherein the C-terminal portion of collagen is selected from the group consisting of pro.alpha.1(I), pro.alpha 2(I), pro.alpha.1(II), pro.alpha.1(III), pro.alpha.1(V), pro.alpha.2(V), pro.alpha.1(XI), pro.alpha.2(XI) and pro.alpha.3(XI)

11. The method of claim 1, wherein the C-terminal portion of collagen comprises a mutated or deleted BMP-1 protease recognition sequence.

12. The method of claim 1, wherein the soluble TNF-alpha receptor is soluble human TNF-alpha receptor.

13. The method of claim 1, wherein the soluble TNF-alpha receptor is selected from the group consisting of soluble p55 TNF-alpha receptor and p75 TNF-alpha receptor.

* * * * *

SEQUENCE LISTING

```
<160> NUMBER OF SEQ ID NOS: 20

<210> SEQ ID NO 1
<211> LENGTH: 963
<212> TYPE: DNA
<213> ORGANISM: Homo sapiens
<220> FEATURE:
<221> NAME/KEY: CDS
<222> LOCATION: (12)...(947)

<400> SEQUENCE: 1
aagcttacgt aagatctaac ggtctccctg gccccattgg gccccctggt cctcgcggtc        60
gcactggtga tgctggtcct gttggtcccc ccggccctcc tggacctcct ggtcccctg       120 gtcctcccag cgctggtttc gacttcagct tcctgcccca gccacctcaa gagaaggctc      180
acgatggtgg ccgctactac cgggctgatg atgccaatgt ggttcgtgac cgtgacctcg      240
aggtggacac caccctcaag agcctgagcc agcagatcga gaacatccgg agcccagagg      300
gaagccgcaa gaaccccgcc cgcacctgcc gtgacctcaa gatgtgccac tctgactgga      360
agagtggaga gtactggatt gaccccaacc aaggctgcaa cctggatgcc atcaaagtct      420
tctgcaacat ggagactggt gagacctgcg tgtaccccac tcagcccagt gtggcccaga      480
agaactggta catcagcaag aaccccaagg acaagaggca tgtctggttc ggcgagagca      540
tgaccgatgg attccagttc gagtatggcg gccagggctc cgaccctgcc gatgtggcca      600
tccagctgac cttcctgcgc ctgatgtcca ccgaggcctc ccagaacatc acctaccact      660
gcaagaacag cgtggcctac atggaccagc agactggcaa cctcaagaag gccctgctcc      720
tcaagggctc caacgagatc gagatccgcg ccgagggcaa cagccgcttc acctacagcg      780
tcactgtcga tggctgcacg agtcacaccg gagcctgggg caagacagtg attgaataca      840
aaaccaccaa gtcctcccgc ctgcccatca tcgatgtggc cccttggac gttggtgccc       900 cagaccagga attcggcttc gacgttggcc ctgtctgctt cctgtaaact ccctccatct      960
aga                                                                    963

<210> SEQ ID NO 2
<211> LENGTH: 311
<212> TYPE: PRT
<213> ORGANISM: Homo sapiens

<400> SEQUENCE: 2

Arg Ser Asn Gly Leu Pro Gly Pro Ile Gly Pro Pro Gly Pro Arg Gly
                 5                  10                  15

Arg Thr Gly Asp Ala Gly Pro Val Gly Pro Pro Gly Pro Pro Gly Pro
            20                  25                  30
```

```
Pro Gly Pro Gly Pro Pro Ser Ala Gly Phe Asp Phe Ser Phe Leu
        35                  40                  45
Pro Gln Pro Pro Gln Glu Lys Ala His Asp Gly Gly Arg Tyr Tyr Arg
 50                  55                  60
Ala Asp Asp Ala Asn Val Val Arg Asp Arg Asp Leu Glu Val Asp Thr
 65                  70                  75                  80
Thr Leu Lys Ser Leu Ser Gln Gln Ile Glu Asn Ile Arg Ser Pro Glu
                 85                  90                  95
Gly Ser Arg Lys Asn Pro Ala Arg Thr Cys Arg Asp Leu Lys Met Cys
                100                 105                 110
His Ser Asp Trp Lys Ser Gly Glu Tyr Trp Ile Asp Pro Asn Gln Gly
                115                 120                 125
Cys Asn Leu Asp Ala Ile Lys Val Phe Cys Asn Met Glu Thr Gly Glu
                130                 135                 140
Thr Cys Val Tyr Pro Thr Gln Pro Ser Val Ala Gln Lys Asn Trp Tyr
145                 150                 155                 160
Ile Ser Lys Asn Pro Lys Asp Lys Arg His Val Trp Phe Gly Glu Ser
                165                 170                 175
Met Thr Asp Gly Phe Gln Phe Glu Tyr Gly Gly Gln Gly Ser Asp Pro
                180                 185                 190
Ala Asp Val Ala Ile Gln Leu Thr Phe Leu Arg Leu Met Ser Thr Glu
                195                 200                 205
Ala Ser Gln Asn Ile Thr Tyr His Cys Lys Asn Ser Val Ala Tyr Met
                210                 215                 220
Asp Gln Gln Thr Gly Asn Leu Lys Lys Ala Leu Leu Leu Lys Gly Ser
225                 230                 235                 240
Asn Glu Ile Glu Ile Arg Ala Glu Gly Asn Ser Arg Phe Thr Tyr Ser
                245                 250                 255
Val Thr Val Asp Gly Cys Thr Ser His Thr Gly Ala Trp Gly Lys Thr
                260                 265                 270
Val Ile Glu Tyr Lys Thr Thr Lys Ser Ser Arg Leu Pro Ile Ile Asp
                275                 280                 285
Val Ala Pro Leu Asp Val Gly Ala Pro Asp Gln Glu Phe Gly Phe Asp
                290                 295                 300
Val Gly Pro Val Cys Phe Leu
305                 310

<210> SEQ ID NO 3
<211> LENGTH: 771
<212> TYPE: DNA
<213> ORGANISM: Homo sapiens
<220> FEATURE:
<221> NAME/KEY: CDS
<222> LOCATION: (12)...(755)

<400> SEQUENCE: 3
aagcttacgt aagatctgat gccaatgtgg ttcgtgaccg tgacctcgag gtggacacca      60
ccctcaagag cctgagccag cagatcgaga catccggag cccagaggga agccgcaaga     120
accccgcccg cacctgccgt gacctcaaga tgtgccactc tgactggaag agtggagagt     180
actggattga ccccaaccaa ggctgcaacc tggatgccat caagtcttc tgcaacatgg     240 agactggtga gacctgcgtg taccccactc agcccagtgt ggcccagaag aactggtaca     300
tcagcaagaa ccccaaggac aagaggcatg tctggttcgg cgagagcatg accgatggat     360
tccagttcga gtatggcggc cagggctccg accctgccga tgtggccatc cagctgacct     420
```

```
tcctgcgcct gatgtccacc gaggcctccc agaacatcac ctaccactgc aagaacagcg    480
tggcctacat ggaccagcag actggcaacc tcaagaaggc cctgctcctc aagggctcca    540
acgagatcga gatccgcgcc gagggcaaca gccgcttcac ctacagcgtc actgtcgatg    600
gctgcacgag tcacaccgga gcctggggca agacagtgat tgaatacaaa accaccaagt    660
cctcccgcct gcccatcatc gatgtggccc ccttggacgt tggtgcccca gaccaggaat    720
tcggcttcga cgttggccct gtctgcttcc tgtaaactcc ctccatctag a            771
```

<210> SEQ ID NO 4
<211> LENGTH: 247
<212> TYPE: PRT
<213> ORGANISM: Homo sapiens

<400> SEQUENCE: 4

```
Arg Ser Asp Ala Asn Val Val Arg Asp Arg Asp Leu Glu Val Asp Thr
1               5                   10                  15

Thr Leu Lys Ser Leu Ser Gln Gln Ile Glu Asn Ile Arg Ser Pro Glu
            20                  25                  30

Gly Ser Arg Lys Asn Pro Ala Arg Thr Cys Arg Asp Leu Lys Met Cys
        35                  40                  45

His Ser Asp Trp Lys Ser Gly Glu Tyr Trp Ile Asp Pro Asn Gln Gly
    50                  55                  60

Cys Asn Leu Asp Ala Ile Lys Val Phe Cys Asn Met Glu Thr Gly Glu
65                  70                  75                  80

Thr Cys Val Tyr Pro Thr Gln Pro Ser Val Ala Gln Lys Asn Trp Tyr
                85                  90                  95

Ile Ser Lys Asn Pro Lys Asp Lys Arg His Val Trp Phe Gly Glu Ser
            100                 105                 110

Met Thr Asp Gly Phe Gln Phe Glu Tyr Gly Gly Gln Gly Ser Asp Pro
        115                 120                 125

Ala Asp Val Ala Ile Gln Leu Thr Phe Leu Arg Leu Met Ser Thr Glu
    130                 135                 140

Ala Ser Gln Asn Ile Thr Tyr His Cys Lys Asn Ser Val Ala Tyr Met
145                 150                 155                 160

Asp Gln Gln Thr Gly Asn Leu Lys Lys Ala Leu Leu Leu Lys Gly Ser
                165                 170                 175

Asn Glu Ile Glu Ile Arg Ala Glu Gly Asn Ser Arg Phe Thr Tyr Ser
            180                 185                 190

Val Thr Val Asp Gly Cys Thr Ser His Thr Gly Ala Trp Gly Lys Thr
        195                 200                 205

Val Ile Glu Tyr Lys Thr Thr Lys Ser Ser Arg Leu Pro Ile Ile Asp
    210                 215                 220

Val Ala Pro Leu Asp Val Gly Ala Pro Asp Gln Glu Phe Gly Phe Asp
225                 230                 235                 240

Val Gly Pro Val Cys Phe Leu
                245
```

<210> SEQ ID NO 5
<211> LENGTH: 2487
<212> TYPE: DNA
<213> ORGANISM: Homo Sapiens
<220> FEATURE:
<221> NAME/KEY: CDS
<222> LOCATION: (12)...(2471)

```
<400> SEQUENCE: 5
aagcttcctg catgctgctg ctgctgctgc tgctgggcct gaggctacag ctctccctgg    60
gcatcatccc agttgaggag gagaacccgg acttctggaa ccgcgaggca gccgaggccc   120
tgggtgccgc caagaagctg cagcctgcac agacagccgc caagaacctc atcatcttcc   180
tgggcgatgg gatggggggtg tctacggtga cagctgccag gatcctaaaa gggcagaaga   240
aggacaaact gggggcctgag ataccctggc catggaccgc ttcccatat gtggctctgt   300
ccaagacata caatgtagac aaacatgtgc cagacagtgg agccacagcc acggcctacc   360
tgtgcggggt caagggcaac ttccagacca ttggcttgag tgcagccgcc cgctttaacc   420
agtgcaacac gacacgcggc aacgaggtca tctccgtgat gaatcgggcc aagaaagcag   480
ggaagtcagt gggagtggta accaccacac gagtgcagca cgcctcgcca gccggcacct   540
acgcccacac ggtgaaccgc aactggtact cggacgccga cgtgcctgcc tcggcccgcc   600
aggagggggtg ccaggacatc gctacgcagc tcatctccaa catggacatt gacgtgatcc   660
taggtggagg ccgaaagtac atgtttccca tgggaacccc agaccctgag tacccagatg   720
actacagcca aggtgggacc aggctggacg ggaagaatct ggtgcaggaa tggctggcga   780
agcgccaggg tgcccggtat gtgtggaacc gcactgagct catgcaggct ccctggacc    840
cgtctgtgac ccatctcatg ggtctctttg agcctggaga catgaaatac gagatccacc   900
gagactccac actggacccc tccctgatgg agatgacaga ggctgccctg cgcctgctga   960
gcaggaaccc ccgcggcttc ttcctcttcg tggagggtgg tcgcatcgac catggtcatc  1020
atgaaagcag ggcttaccgg gcactgactg agacgatcat gttcgacgac gccattgaga  1080
gggcgggcca gctcaccagc gaggaggaca cgctgagcct cgtcactgcc gaccactccc  1140
acgtcttctc cttcggaggc taccccctgc gagggagctc catcttcggg ctggcccctg  1200
gcaaggcccg ggacaggaag gcctacacgg tcctcctata cggaaacggt ccaggctatg  1260
tgctcaagga cggcgcccgg ccggatgtta ccgagagcga gagcgggagc cccgagtatc  1320
ggcagcagtc agcagtgccc ctggacgaag agacccacgc aggcgaggac gtggcggtgt  1380
tcgcgcgcgg cccgcaggcg cacctggttc acggcgtgca ggagcagacc ttcatagcgc  1440
acgtcatggc cttcgccgcc tgcctggagc cctacaccgc ctgcgacctg gcgcccccg   1500
ccggcaccac cgacgccgcg cacccgggtt ccggaagatc taacggtctc cctggcccca  1560
ttgggccccc tggtcctcgc ggtcgcactg gtgatgctgg tcctgttggt cccccggcc   1620
ctcctggacc tcctggtccc cctggtcctc ccagcgctgg tttcgacttc agcttcctgc  1680
cccagccacc tcaagagaag gctcacgatg tggccgcta ctaccgggct gatgatgcca   1740
atgtggttcg tgaccgtgac ctcgaggtgg acaccaccct caagagcctg agccagcaga  1800
tcgagaacat ccggagccca gagggaagcc gcaagaaccc cgcccgcacc tgccgtgacc  1860
tcaagatgtg ccactctgac tggaagagtg gagagtactg gattgacccc aaccaaggct  1920
gcaacctgga tgccatcaaa gtcttctgca acatggagac tggtgagacc tgcgtgtacc  1980
ccactcagcc cagtgtggcc cagaagaact ggtacatcag caagaacccc aaggacaaga  2040
ggcatgtctg gttcggcgag agcatgaccg atggattcca gttcgagtat ggcggccagg  2100
gctccgaccc tgccgatgtg gccatccagc tgaccttcct cgcgctgatg tccaccgagg  2160
cctcccagaa catcacctac cactgcaaga acagcgtggc ctacatggac cagcagactg  2220
gcaacctcaa gaaggccctg ctcctcaagg ctccaacga gatcgagatc cgcgccgagg  2280
gcaacagccg cttcacctac agcgtcactg tcgatggctg cacgagtcac accggagcct  2340
```

```
gggggcaagac agtgattgaa tacaaaacca ccaagtcctc ccgcctgccc atcatcgatg    2400 tggcccccctt ggacgttggt gccccagacc aggaattcgg cttcgacgtt ggccctgtct    2460
gcttcctgta aactccctcc atctaga                                         2487
```

<210> SEQ ID NO 6
<211> LENGTH: 819
<212> TYPE: PRT
<213> ORGANISM: Homo Sapiens

<400> SEQUENCE: 6

```
Met Leu Leu Leu Leu Leu Leu Gly Leu Arg Leu Gln Leu Ser Leu
                 5                  10                  15

Gly Ile Ile Pro Val Glu Glu Glu Asn Pro Asp Phe Trp Asn Arg Glu
                 20                  25                  30

Ala Glu Ala Leu Gly Ala Ala Lys Lys Leu Gln Pro Ala Gln Thr
             35                  40                  45

Ala Ala Lys Asn Leu Ile Ile Phe Leu Gly Asp Gly Met Gly Val Ser
         50                  55                  60

Thr Val Thr Ala Ala Arg Ile Leu Lys Gly Gln Lys Lys Asp Lys Leu
65                  70                  75                  80

Gly Pro Glu Ile Pro Leu Ala Met Asp Arg Phe Pro Tyr Val Ala Leu
                 85                  90                  95

Ser Lys Thr Tyr Asn Val Asp Lys His Val Pro Asp Ser Gly Ala Thr
             100                 105                 110

Ala Thr Ala Tyr Leu Cys Gly Val Lys Gly Asn Phe Gln Thr Ile Gly
         115                 120                 125

Leu Ser Ala Ala Ala Arg Phe Asn Gln Cys Asn Thr Thr Arg Gly Asn
     130                 135                 140

Glu Val Ile Ser Val Met Asn Arg Ala Lys Lys Ala Gly Lys Ser Val
145                 150                 155                 160

Gly Val Val Thr Thr Thr Arg Val Gln His Ala Ser Pro Ala Gly Thr
                 165                 170                 175

Tyr Ala His Thr Val Asn Arg Asn Trp Tyr Ser Asp Ala Asp Val Pro
             180                 185                 190

Ala Ser Ala Arg Gln Glu Gly Cys Gln Asp Ile Ala Thr Gln Leu Ile
         195                 200                 205

Ser Asn Met Asp Ile Asp Val Ile Leu Gly Gly Gly Arg Lys Tyr Met
     210                 215                 220

Phe Pro Met Gly Thr Pro Asp Pro Glu Tyr Pro Asp Asp Tyr Ser Gln
225                 230                 235                 240

Gly Gly Thr Arg Leu Asp Gly Lys Asn Leu Val Gln Glu Trp Leu Ala
                 245                 250                 255

Lys Arg Gln Gly Ala Arg Tyr Val Trp Asn Arg Thr Glu Leu Met Gln
             260                 265                 270

Ala Ser Leu Asp Pro Ser Val Thr His Leu Met Gly Leu Phe Glu Pro
         275                 280                 285

Gly Asp Met Lys Tyr Glu Ile His Arg Asp Ser Thr Leu Asp Pro Ser
     290                 295                 300

Leu Met Glu Met Thr Glu Ala Ala Leu Arg Leu Leu Ser Arg Asn Pro
305                 310                 315                 320

Arg Gly Phe Phe Leu Phe Val Glu Gly Gly Arg Ile Asp His Gly His
                 325                 330                 335

His Glu Ser Arg Ala Tyr Arg Ala Leu Thr Glu Thr Ile Met Phe Asp
             340                 345                 350
```

-continued

```
Asp Ala Ile Glu Arg Ala Gly Gln Leu Thr Ser Glu Glu Asp Thr Leu
        355                 360                 365

Ser Leu Val Thr Ala Asp His Ser His Val Phe Ser Phe Gly Gly Tyr
    370                 375                 380

Pro Leu Arg Gly Ser Ser Ile Phe Gly Leu Ala Pro Gly Lys Ala Arg
385                 390                 395                 400

Asp Arg Lys Ala Tyr Thr Val Leu Leu Tyr Gly Asn Gly Pro Gly Tyr
                405                 410                 415

Val Leu Lys Asp Gly Ala Arg Pro Asp Val Thr Glu Ser Glu Ser Gly
            420                 425                 430

Ser Pro Glu Tyr Arg Gln Gln Ser Ala Val Pro Leu Asp Glu Glu Thr
        435                 440                 445

His Ala Gly Glu Asp Val Ala Val Phe Ala Arg Gly Pro Gln Ala His
    450                 455                 460

Leu Val His Gly Val Gln Glu Gln Thr Phe Ile Ala His Val Met Ala
465                 470                 475                 480

Phe Ala Ala Cys Leu Glu Pro Tyr Thr Ala Cys Asp Leu Ala Pro Pro
                485                 490                 495

Ala Gly Thr Thr Asp Ala Ala His Pro Gly Ser Gly Arg Ser Asn Gly
            500                 505                 510

Leu Pro Gly Pro Ile Gly Pro Gly Pro Arg Gly Arg Thr Gly Asp
        515                 520                 525

Ala Gly Pro Val Gly Pro Pro Gly Pro Pro Gly Pro Pro Gly Pro Pro
    530                 535                 540

Gly Pro Pro Ser Ala Gly Phe Asp Phe Ser Phe Leu Pro Gln Pro Pro
545                 550                 555                 560

Gln Glu Lys Ala His Asp Gly Gly Arg Tyr Tyr Arg Ala Asp Asp Ala
                565                 570                 575

Asn Val Val Arg Asp Arg Asp Leu Glu Val Asp Thr Thr Leu Lys Ser
            580                 585                 590

Leu Ser Gln Gln Ile Glu Asn Ile Arg Ser Pro Glu Gly Ser Arg Lys
        595                 600                 605

Asn Pro Ala Arg Thr Cys Arg Asp Leu Lys Met Cys His Ser Asp Trp
    610                 615                 620

Lys Ser Gly Glu Tyr Trp Ile Asp Pro Asn Gln Gly Cys Asn Leu Asp
625                 630                 635                 640

Ala Ile Lys Val Phe Cys Asn Met Glu Thr Gly Glu Thr Cys Val Tyr
                645                 650                 655

Pro Thr Gln Pro Ser Val Ala Gln Lys Asn Trp Tyr Ile Ser Lys Asn
            660                 665                 670

Pro Lys Asp Lys Arg His Val Trp Phe Gly Glu Ser Met Thr Asp Gly
        675                 680                 685

Phe Gln Phe Glu Tyr Gly Gly Gln Gly Ser Asp Pro Ala Asp Val Ala
    690                 695                 700

Ile Gln Leu Thr Phe Leu Arg Leu Met Ser Thr Glu Ala Ser Gln Asn
705                 710                 715                 720

Ile Thr Tyr His Cys Lys Asn Ser Val Ala Tyr Met Asp Gln Gln Thr
                725                 730                 735

Gly Asn Leu Lys Lys Ala Leu Leu Leu Lys Gly Ser Asn Glu Ile Glu
            740                 745                 750

Ile Arg Ala Glu Gly Asn Ser Arg Phe Thr Tyr Ser Val Thr Val Asp
        755                 760                 765
```

```
Gly Cys Thr Ser His Thr Gly Ala Trp Gly Lys Thr Val Ile Glu Tyr
        770                 775                 780

Lys Thr Thr Lys Ser Ser Arg Leu Pro Ile Ile Asp Val Ala Pro Leu
785                 790                 795                 800

Asp Val Gly Ala Pro Asp Gln Glu Phe Gly Phe Asp Val Gly Pro Val
                805                 810                 815

Cys Phe Leu
        819

<210> SEQ ID NO 7
<211> LENGTH: 2294
<212> TYPE: DNA
<213> ORGANISM: Homo Sapiens
<220> FEATURE:
<221> NAME/KEY: CDS
<222> LOCATION: (12)...(2278)

<400> SEQUENCE: 7
```

| | |
|---|---:|
| aagcttcctg catgctgctg ctgctgctgc tgctgggcct gaggctacag ctctccctgg | 60 |
| gcatcatccc agttgaggag gagaacccgg acttctggaa ccgcgaggca gccgaggccc | 120 |
| tgggtgccgc caagaagctg cagcctgcac agacagccgc caagaacctc atcatcttcc | 180 |
| tgggcgatgg gatgggggtg tctacggtga cagctgccag gatcctaaaa gggcagaaga | 240 |
| aggacaaact ggggcctgag ataccctggg ccatggaccg cttcccatat gtggctctgt | 300 |
| ccaagacata caatgtagac aaacatgtgc agacagtgg agccacagcc acggcctacc | 360 |
| tgtgcggggt caagggcaac ttccagacca ttggcttgag tgcagccgcc cgctttaacc | 420 |
| agtgcaacac gacacgcggc aacgaggtca tctccgtgat gaatcgggcc aagaaagcag | 480 |
| ggaagtcagt gggagtggta accaccacac gagtgcagca cgcctcgcca gccggcacct | 540 |
| acgcccacac ggtgaaccgc aactggtact cggacgccga cgtgcctgcc tcggcccgcc | 600 |
| aggaggggtg ccaggacatc gctacgcagc tcatctccaa catggacatt gacgtgatcc | 660 |
| taggtggagg ccgaaagtac atgtttccca tgggaacccc agaccctgag tacccagatg | 720 |
| actacagcca aggtgggacc aggctggacg ggaagaatct ggtgcaggaa tggctggcga | 780 |
| agcgccaggg tgcccggtat gtgtggaacc gcactgagct catgcaggct tccctggacc | 840 |
| cgtctgtgac ccatctcatg ggtctctttg agcctggaga catgaaatac gagatccacc | 900 |
| gagactccac actggacccc tccctgatgg agatgacaga ggctgccctg cgcctgctga | 960 |
| gcaggaaccc ccgcggcttc ttcctcttcg tggagggtgg tcgcatcgac catggtcatc | 1020 |
| atgaaagcag ggcttaccgg gcactgactg agacgatcat gttcgacgac gccattgaga | 1080 |
| gggcgggcca gctcaccagc gaggaggaca cgctgagcct cgtcactgcc gaccactccc | 1140 |
| acgtcttctc cttcggaggc taccccctgc gagggagctc catcttcggg ctggccctg | 1200 |
| gcaaggcccg ggacaggaag gcctacacgg tcctcctata cggaaacggt ccaggctatg | 1260 |
| tgctcaagga cggcgcccgg ccggatgtta ccgagagcga gagcgggagc cccgagtatc | 1320 |
| ggcagcagtc agcagtgccc ctggacgaag agacccacgc aggcgaggac gtggcggtgt | 1380 |
| tcgcgcgcgg cccgcaggcg cacctggttc acggcgtgca ggagcagacc ttcatagcgc | 1440 |
| acgtcatggc cttcgccgcc tgcctggagc cctacaccgc ctgcgacctg gcgcccccg | 1500 |
| ccggcaccac cgacgccgcg cacccggggt tccgagatct gatgccaatg tggttcgtga | 1560 |
| ccgtgacctc gaggtggaca ccaccctcaa gagcctgagc cagcagatcg agaacatccg | 1620 |
| gagcccagag ggaagccgca agaacccgc ccgcacctgc cgtgacctca agatgtgcca | 1680 |

-continued

```
ctctgactgg aagagtggag agtactggat tgaccccaac caaggctgca acctggatgc    1740
catcaaagtc ttctgcaaca tggagactgg tgagacctgc gtgtacccca ctcagcccag    1800
tgtggcccag aagaactggt acatcagcaa gaacccaagg acaagaggc atgtctggtt     1860 cggcgagagc atgaccgatg gattccagtt cgagtatggc ggccagggct ccgaccctgc    1920
cgatgtggcc atccagctga ccttcctgcg cctgatgtcc accgaggcct cccagaacat    1980
cacctaccac tgcaagaaca cgtggcctca catggaccag cagactggca acctcaagaa    2040
ggccctgctc ctcaagggct ccaacgagat cgagatccgc gccgagggca acagccgctt    2100
cacctacagc gtcactgtcg atggctgcac gagtcacacc ggagcctggg gcaagacagt    2160
gattgaatac aaaaccacca gtcctcccg cctgcccatc atcgatgtgg cccccttgga    2220
cgttggtgcc ccagaccagg aattcggctt cgacgttggc cctgtctgct tcctgtaaac    2280
tccctccatc taga                                                      2294
```

<210> SEQ ID NO 8
<211> LENGTH: 755
<212> TYPE: PRT
<213> ORGANISM: Homo Sapiens

<400> SEQUENCE: 8

```
Met Leu Leu Leu Leu Leu Leu Gly Leu Arg Leu Gln Leu Ser Leu
1               5                   10                  15

Gly Ile Ile Pro Val Glu Glu Asn Pro Asp Phe Trp Asn Arg Glu
                20                  25                  30

Ala Glu Ala Leu Gly Ala Ala Lys Lys Leu Gln Pro Ala Gln Thr
            35                  40                  45

Ala Ala Lys Asn Leu Ile Ile Phe Leu Gly Asp Gly Met Gly Val Ser
        50                  55                  60

Thr Val Thr Ala Ala Arg Ile Leu Lys Gly Gln Lys Lys Asp Lys Leu
65                  70                  75                  80

Gly Pro Glu Ile Pro Leu Ala Met Asp Arg Phe Pro Tyr Val Ala Leu
                85                  90                  95

Ser Lys Thr Tyr Asn Val Asp Lys His Val Pro Asp Ser Gly Ala Thr
            100                 105                 110

Ala Thr Ala Tyr Leu Cys Gly Val Lys Gly Asn Phe Gln Thr Ile Gly
        115                 120                 125

Leu Ser Ala Ala Ala Arg Phe Asn Gln Cys Asn Thr Thr Arg Gly Asn
130                 135                 140

Glu Val Ile Ser Val Met Asn Arg Ala Lys Lys Ala Gly Lys Ser Val
145                 150                 155                 160

Gly Val Val Thr Thr Thr Arg Val Gln His Ala Ser Pro Ala Gly Thr
                165                 170                 175

Tyr Ala His Thr Val Asn Arg Asn Trp Tyr Ser Asp Ala Asp Val Pro
            180                 185                 190

Ala Ser Ala Arg Gln Glu Gly Cys Gln Asp Ile Ala Thr Gln Leu Ile
        195                 200                 205

Ser Asn Met Asp Ile Asp Val Ile Leu Gly Gly Gly Arg Lys Tyr Met
210                 215                 220

Phe Pro Met Gly Thr Pro Asp Pro Glu Tyr Pro Asp Asp Tyr Ser Gln
225                 230                 235                 240

Gly Gly Thr Arg Leu Asp Gly Lys Asn Leu Val Gln Glu Trp Leu Ala
                245                 250                 255
```

-continued

```
Lys Arg Gln Gly Ala Arg Tyr Val Trp Asn Arg Thr Glu Leu Met Gln
                260                 265                 270

Ala Ser Leu Asp Pro Ser Val Thr His Leu Met Gly Leu Phe Glu Pro
            275                 280                 285

Gly Asp Met Lys Tyr Glu Ile His Arg Asp Ser Thr Leu Asp Pro Ser
        290                 295                 300

Leu Met Glu Met Thr Glu Ala Ala Leu Arg Leu Leu Ser Arg Asn Pro
305                 310                 315                 320

Arg Gly Phe Phe Leu Phe Val Glu Gly Gly Arg Ile Asp His Gly His
                325                 330                 335

His Glu Ser Arg Ala Tyr Arg Ala Leu Thr Glu Thr Ile Met Phe Asp
            340                 345                 350

Asp Ala Ile Glu Arg Ala Gly Gln Leu Thr Ser Glu Glu Asp Thr Leu
        355                 360                 365

Ser Leu Val Thr Ala Asp His Ser His Val Phe Ser Phe Gly Gly Tyr
370                 375                 380

Pro Leu Arg Gly Ser Ser Ile Phe Gly Leu Ala Pro Gly Lys Ala Arg
385                 390                 395                 400

Asp Arg Lys Ala Tyr Thr Val Leu Leu Tyr Gly Asn Gly Pro Gly Tyr
                405                 410                 415

Val Leu Lys Asp Gly Ala Arg Pro Asp Val Thr Glu Ser Glu Ser Gly
            420                 425                 430

Ser Pro Glu Tyr Arg Gln Gln Ser Ala Val Pro Leu Asp Glu Glu Thr
        435                 440                 445

His Ala Gly Glu Asp Val Ala Val Phe Ala Arg Gly Pro Gln Ala His
450                 455                 460

Leu Val His Gly Val Gln Glu Gln Thr Phe Ile Ala His Val Met Ala
465                 470                 475                 480

Phe Ala Ala Cys Leu Glu Pro Tyr Thr Ala Cys Asp Leu Ala Pro Pro
                485                 490                 495

Ala Gly Thr Thr Asp Ala Ala His Pro Gly Ser Gly Arg Ser Asp Ala
            500                 505                 510

Asn Val Val Arg Asp Arg Asp Leu Glu Val Asp Thr Thr Leu Lys Ser
        515                 520                 525

Leu Ser Gln Gln Ile Glu Asn Ile Arg Ser Pro Glu Gly Ser Arg Lys
530                 535                 540

Asn Pro Ala Arg Thr Cys Arg Asp Leu Lys Met Cys His Ser Asp Trp
545                 550                 555                 560

Lys Ser Gly Glu Tyr Trp Ile Asp Pro Asn Gln Gly Cys Asn Leu Asp
                565                 570                 575

Ala Ile Lys Val Phe Cys Asn Met Glu Thr Gly Glu Thr Cys Val Tyr
            580                 585                 590

Pro Thr Gln Pro Ser Val Ala Gln Lys Asn Trp Tyr Ile Ser Lys Asn
        595                 600                 605

Pro Lys Asp Lys Arg His Val Trp Phe Gly Glu Ser Met Thr Asp Gly
610                 615                 620

Phe Gln Phe Glu Tyr Gly Gly Gln Gly Ser Asp Pro Ala Asp Val Ala
625                 630                 635                 640

Ile Gln Leu Thr Phe Leu Arg Leu Met Ser Thr Glu Ala Ser Gln Asn
                645                 650                 655

Ile Thr Tyr His Cys Lys Asn Ser Val Ala Tyr Met Asp Gln Gln Thr
            660                 665                 670
```

-continued

```
Gly Asn Leu Lys Lys Ala Leu Leu Lys Gly Ser Asn Glu Ile Glu
            675                 680                 685

Ile Arg Ala Glu Gly Asn Ser Arg Phe Thr Tyr Ser Val Thr Val Asp
        690                 695                 700

Gly Cys Thr Ser His Thr Gly Ala Trp Gly Lys Thr Val Ile Glu Tyr
705                 710                 715                 720

Lys Thr Thr Lys Ser Ser Arg Leu Pro Ile Ile Asp Val Ala Pro Leu
                725                 730                 735

Asp Val Gly Ala Pro Asp Gln Glu Phe Gly Phe Asp Val Gly Pro Val
            740                 745                 750

Cys Phe Leu
        755

<210> SEQ ID NO 9
<211> LENGTH: 1734
<212> TYPE: DNA
<213> ORGANISM: Artificial
<220> FEATURE:
<221> NAME/KEY: CDS
<222> LOCATION: (18)...(1718)
<223> OTHER INFORMATION: Nucleotide Sequence Encoding sTNF-RII-TO Fusion
      Polypeptide

<400> SEQUENCE: 9
ggatcccgcc cgcacccatg gcgcccgtcg ccgtctgggc gcgctggccc gtcggactgg      60
agctctgggc tgcggcgcac gccttgcccg cccaggtggc atttacaccc tacgccccgg     120
agcccgggag cacatgccgg ctcagagaat actatgacca gacagctcag atgtgctgca     180
gcaaatgctc gccgggccaa catgcaaaag tcttctgtac caagacctcg gacaccgtgt     240
gtgactcctg tgaggacagc acatacaccc agctctggaa ctgggttccc gagtgcttga     300
gctgtggctc ccgctgtagc tctgaccagg tggaaactca agcctgcact cgggaacaga     360
accgcatctg cacctgcagg cccggctggt actgcgcgct gagcaagcag agggggtgcc     420
ggctgtgcgc gccgctgcgc aagtgccgcc cgggcttcgg cgtggccaga ccaggaactg     480
aaacatcaga cgtggtgtgc aagccctgtg ccccggggac gttctccaac acgacttcat     540
ccacggatat ttgcaggccc caccagatct gtaacgtggt ggccatccct gggaatgcaa     600
gcatggatgc agtctgcacg tccacgtccc cacccggag tatggcccca ggggcagtac     660
acttaccccg ccagtgtcc acacgatccc aacacacgca gccaactcca gaacccagca     720
ctgctccaag cacctccttc ctgctcccaa tgggccccag ccccccagct gaagggagca     780
ctggatctaa cggtctccct ggccccattg gccccctgg tcctcgcggt cgcactggtg     840
atgctggtcc tgttggtccc ccggccctc ctggacctcc tggtcccct ggtcctccca     900 gcgctggttt cgacttcagc ttcctgcccc agccacctca agagaaggct cacgatggtg     960
gccgctacta ccgggctgat gatgccaatg tggttcgtga ccgtgacctc gaggtggaca    1020
ccaccctcaa gagcctgagc agcagatcg agaacatccg gagcccagag gaagccgca    1080 agaaccccgc ccgcacctgc cgtgacctca gatgtgcca ctctgactgg aagagtggag    1140
agtactggat tgaccccaac caaggctgca acctggatgc atcaaagtc ttctgcaaca    1200 tggagactgg tgagacctgc gtgtacccca ctcagcccag tgtgccccag aagaactggt    1260
acatcagcaa gaaccccaag gacaagaggc atgtctggtt cggcgagagc atgaccgatg    1320
gattccagtt cgagtatggc ggccagggct ccgaccctgc cgatgtggcc atccagctga    1380
ccttcctgcg cctgatgtcc accgaggcct cccagaacat cacctaccac tgcaagaaca    1440
```

-continued

```
gcgtggccta catggaccag cagactggca acctcaagaa ggccctgctc ctcaagggct    1500
ccaacgagat cgagatccgc gccgagggca acagccgctt cacctacagc gtcactgtcg    1560
atggctgcac gagtcacacc ggagcctggg gcaagacagt gattgaatac aaaaccacca    1620
agtcctcccg cctgcccatc atcgatgtgg ccccttgga cgttggtgcc ccagaccagg    1680
aattcggctt cgacgttggc cctgtctgct tcctgtaaac tccctccatc taga          1734
```

<210> SEQ ID NO 10
<211> LENGTH: 566
<212> TYPE: PRT
<213> ORGANISM: Artificial
<220> FEATURE:
<223> OTHER INFORMATION: sTNF-RII-TO Fusion Polypeptide

<400> SEQUENCE: 10

```
Met Ala Pro Val Ala Val Trp Ala Ala Leu Ala Val Gly Leu Glu Leu
              5                  10                  15

Trp Ala Ala His Ala Leu Pro Ala Gln Val Ala Phe Thr Pro Tyr
         20                  25                  30

Ala Pro Glu Pro Gly Ser Thr Cys Arg Leu Arg Glu Tyr Tyr Asp Gln
         35                  40                  45

Thr Ala Gln Met Cys Cys Ser Lys Cys Ser Pro Gly Gln His Ala Lys
     50                  55                  60

Val Phe Cys Thr Lys Thr Ser Asp Thr Val Cys Asp Ser Cys Glu Asp
 65                  70                  75                  80

Ser Thr Tyr Thr Gln Leu Trp Asn Trp Val Pro Glu Cys Leu Ser Cys
                 85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Pro Ala Glu Gly Ser Thr Gly
                245                 250                 255

Ser Asn Gly Leu Pro Gly Pro Ile Gly Pro Gly Pro Arg Gly Arg
            260                 265                 270

Thr Gly Asp Ala Gly Pro Val Gly Pro Pro Gly Pro Pro Gly Pro Pro
        275                 280                 285

Gly Pro Pro Gly Pro Pro Ser Ala Gly Phe Asp Phe Ser Phe Leu Pro
    290                 295                 300

Gln Pro Pro Gln Glu Lys Ala His Asp Gly Gly Arg Tyr Tyr Arg Ala
305                 310                 315                 320
```

-continued

```
Asp Asp Ala Asn Val Val Arg Asp Arg Asp Leu Glu Val Asp Thr Thr
            325                 330                 335

Leu Lys Ser Leu Ser Gln Gln Ile Glu Asn Ile Arg Ser Pro Gly Gly
            340                 345                 350

Ser Arg Lys Asn Pro Ala Arg Thr Cys Arg Asp Leu Lys Met Cys His
            355                 360                 365

Ser Asp Trp Lys Ser Gly Glu Tyr Trp Ile Asp Pro Asn Gln Gly Cys
    370                 375                 380

Asn Leu Asp Ala Ile Lys Val Phe Cys Asn Met Glu Thr Gly Glu Thr
385                 390                 395                 400

Cys Val Tyr Pro Thr Gln Pro Ser Val Ala Gln Lys Asn Trp Tyr Ile
                405                 410                 415

Ser Lys Asn Pro Lys Asp Lys Arg His Val Trp Phe Gly Glu Ser Met
            420                 425                 430

Thr Asp Gly Phe Gln Phe Glu Tyr Gly Gly Gln Gly Ser Asp Pro Ala
            435                 440                 445

Asp Val Ala Ile Gln Leu Thr Phe Leu Arg Leu Met Ser Thr Glu Ala
    450                 455                 460

Ser Gln Asn Ile Thr Tyr His Cys Lys Asn Ser Val Ala Tyr Met Asp
465                 470                 475                 480

Gln Gln Thr Gly Asn Leu Lys Lys Ala Leu Leu Leu Lys Gly Ser Asn
                485                 490                 495

Glu Ile Glu Ile Arg Ala Glu Gly Asn Ser Arg Phe Thr Tyr Ser Val
            500                 505                 510

Thr Val Asp Gly Cys Thr Ser His Thr Gly Ala Trp Gly Lys Thr Val
            515                 520                 525

Ile Glu Tyr Lys Thr Thr Lys Ser Ser Arg Leu Pro Ile Ile Asp Val
    530                 535                 540

Ala Pro Leu Asp Val Gly Ala Pro Asp Gln Glu Phe Gly Phe Asp Val
545                 550                 555                 560

Gly Pro Val Cys Phe Leu
                565
```

```
<210> SEQ ID NO 11
<211> LENGTH: 1542
<212> TYPE: DNA
<213> ORGANISM: Artificial
<220> FEATURE:
<221> NAME/KEY: CDS
<222> LOCATION: (18)...(1526)
<223> OTHER INFORMATION: Nucleotide Sequence Encoding sTNF-RII-T2 Fusion
      Polypeptide

<400> SEQUENCE: 11
```

```
ggatcccgcc cgcacccatg gcgcccgtcg ccgtctgggc cgcgctggcc gtcggactgg      60
agctctgggc tgcggcgcac gccttgcccg cccaggtggc atttacaccc tacgccccgg     120
agcccgggag cacatgccgg ctcagagaat actatgacca gacagctcag atgtgctgca    180
gcaaatgctc gccgggccaa catgcaaaag tcttctgtac caagacctcg gacaccgtgt    240
gtgactcctg tgaggacagc acatacaccc agctctggaa ctgggttccc gagtgcttga    300
gctgtggctc ccgctgtagc tctgaccagg tggaaactca agcctgcact cgggaacaga    360
accgcatctg cacctgcagg cccggctggt actgcgcgct gagcaagcag gagggtgcc     420 ggctgtgcgc gccgctgcgc aagtgccgcc cgggcttcgg cgtggccaga ccaggaactg    480
aaacatcaga cgtggtgtgc aagccctgtg ccccggggac gttctccaac acgacttcat    540
```

```
ccacggatat tgcaggcccc caccagatct gtaacgtggt ggccatccct gggaatgcaa      600
gcatggatgc agtctgcacg tccacgtccc ccacccggag tatggcccca ggggcagtac      660
acttacccca gccagtgtcc acacgatccc aacacacgca gccaactcca gaacccagca      720
ctgctccaag cacctccttc ctgctcccaa tgggccccag cccccagct gaagggagca       780 ctggatctga tgccaatgtg gttcgtgacc gtgacctcga ggtggacacc accctcaaga      840
gcctgagcca gcagatcgag aacatccgga gcccagaggg aagccgcaag aaccccgccc      900
gcacctgccg tgacctcaag atgtgccact ctgactggaa gagtggagag tactggattg      960
accccaacca aggctgcaac ctggatgcca tcaaagtctt ctgcaacatg gagactggtg     1020
agacctgcgt gtaccccact cagcccagtg tggcccagaa gaactggtac atcagcaaga     1080
accccaagga caagaggcat gtctggttcg gcgagagcat gaccgatgga ttccagttcg     1140
agtatggcgg ccagggctcc gaccctgccg atgtggccat ccagctgacc ttcctgcgcc     1200
tgatgtccac cgaggcctcc cagaacatca cctaccactg caagaacagc gtggcctaca     1260
tggaccagca gactggcaac ctcaagaagg ccctgctcct caagggctcc aacgagatcg     1320
agatccgcgc cgagggcaac agccgcttca cctacagcgt cactgtcgat ggctgcacga     1380
gtcacaccgg agcctggggc aagacagtga ttgaataca aaccaccaag tcctcccgcc      1440 tgccatcat cgatgtggcc cccttggacg ttggtgcccc agaccaggaa ttcggcttcg      1500
acgttggccc tgtctgcttc ctgtaaactc cctccatcta ga                       1542

<210> SEQ ID NO 12
<211> LENGTH: 502
<212> TYPE: PRT
<213> ORGANISM: Artificial
<220> FEATURE:
<223> OTHER INFORMATION: sTNF-RII-T2 Fusion Polypeptide

<400> SEQUENCE: 12

Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
                20                  25                  30

Ala Pro Glu Pro Gly Ser Thr Cys Arg Leu Arg Glu Tyr Tyr Asp Gln
            35                  40                  45

Thr Ala Gln Met Cys Cys Ser Lys Cys Ser Pro Gly Gln His Ala Lys
        50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190
```

```
Asn Ala Ser Met Asp Ala Val Cys Thr Ser Thr Ser Pro Thr Arg Ser
            195                 200                 205

Met Ala Pro Gly Ala Val His Leu Pro Gln Pro Val Ser Thr Arg Ser
        210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Ala Glu Gly Ser Thr Gly
                245                 250                 255

Ser Asp Ala Asn Val Val Arg Asp Arg Asp Leu Glu Val Asp Thr Thr
                260                 265                 270

Leu Lys Ser Leu Ser Gln Gln Ile Glu Asn Ile Arg Ser Pro Glu Gly
            275                 280                 285

Ser Arg Lys Asn Pro Ala Arg Thr Cys Arg Asp Leu Lys Met Cys His
        290                 295                 300

Ser Asp Trp Lys Ser Gly Glu Tyr Trp Ile Asp Pro Asn Gln Gly Cys
305                 310                 315                 320

Asn Leu Asp Ala Ile Lys Val Phe Cys Asn Met Glu Thr Gly Glu Thr
                325                 330                 335

Cys Val Tyr Pro Thr Gln Pro Ser Val Ala Gln Lys Asn Trp Tyr Ile
                340                 345                 350

Ser Lys Asn Pro Lys Asp Lys Arg His Val Trp Phe Gly Glu Ser Met
            355                 360                 365

Thr Asp Gly Phe Gln Phe Glu Tyr Gly Gly Gln Gly Ser Asp Pro Ala
        370                 375                 380

Asp Val Ala Ile Gln Leu Thr Phe Leu Arg Leu Met Ser Thr Glu Ala
385                 390                 395                 400

Ser Gln Asn Ile Thr Tyr His Cys Lys Asn Ser Val Ala Tyr Met Asp
                405                 410                 415

Gln Gln Thr Gly Asn Leu Lys Lys Ala Leu Leu Leu Lys Gly Ser Asn
            420                 425                 430

Glu Ile Glu Ile Arg Ala Glu Gly Asn Ser Arg Phe Thr Tyr Ser Val
        435                 440                 445

Thr Val Asp Gly Cys Thr Ser His Thr Gly Ala Trp Gly Lys Thr Val
    450                 455                 460

Ile Glu Tyr Lys Thr Thr Lys Ser Ser Arg Leu Pro Ile Ile Asp Val
465                 470                 475                 480

Ala Pro Leu Asp Val Gly Ala Pro Asp Gln Glu Phe Gly Phe Asp Val
                485                 490                 495

Gly Pro Val Cys Phe Leu
            500

<210> SEQ ID NO 13
<211> LENGTH: 2139
<212> TYPE: DNA
<213> ORGANISM: Artificial
<220> FEATURE:
<221> NAME/KEY: CDS
<222> LOCATION: (24)...(2123)
<223> OTHER INFORMATION: Nucleotide Sequence Encoding CD4-TO Fusion
      Polypeptide

<400> SEQUENCE: 13
aagcttccct cggcaaggcc acaatgaacc ggggagtccc ttttaggcac ttgcttctgg      60
tgctgcaact ggcgctcctc ccagcagcca ctcaggaaa gaaagtggtg ctgggcaaaa     120
aaggggatac agtggaactg acctgtacag cttcccagaa gaagagcata caattccact     180
```

-continued

```
ggaaaaactc caaccagata aagattctgg gaaatcaggg ctccttctta actaaaggtc    240
catccaagct gaatgatcgc gctgactcaa gaagaagcct ttgggaccaa ggaaactttc    300
ccctgatcat caagaatctt aagatagaag actcagatac ttacatctgt gaagtggagg    360
accagaagga ggaggtgcaa ttgctagtgt tcggattgac tgccaactct gacacccacc    420
tgcttcaggg gcagagcctg accctgacct tggagagccc cctggtagt agcccctcag    480 tgcaatgtag gagtccaagg ggtaaaaaca tacagggggg aagaccctc tccgtgtctc    540 agctggagct ccaggatagt ggcacctgga catgcactgt cttgcagaac agaagaagg    600 tggagttcaa aatagacatc gtggtgctag cttccagaa ggcctccagc atagtctata    660
agaaagaggg ggaacaggtg gagttctcct tcccactcgc cttacagtt gaaaagctga    720 cgggcagtgg cgagctgtgg tggcaggcgg agagggcttc ctcctccaag tcttggatca    780
cctttgacct gaagaacaag gaagtgtctg taaaacgggt tacccaggac cctaagctcc    840
agatgggcaa gaagctcccg ctccacctca ccctgcccca ggccttgcct cagtatgctg    900
gctctggaaa cctcaccctg gcccttgaag cgaaaacagg aaagttgcat caggaagtga    960
acctggtggt gatgagagcc actcagctcc agaaaaattt gacctgtgag gtgtggggac    1020
ccacctcccc taagctgatg ctgagcttga actggagaca aggaggca aaggtctcga    1080 agcgggagaa ggcggtgtgg gtgctgaacc ctgaggcggg gatgtggcag tgtctgctga    1140
gtgactcggg acaggtcctg ctggaatcca acatcaaggt tctgcccaga tctaacggtc    1200
tccctggccc cattgggccc cctggtcctc gcggtcgcac tggtgatgct ggtcctgttg    1260
gtccccccgg ccctcctgga cctcctggtc cccctggtcc tcccagcgct ggtttcgact    1320
tcagcttcct gccccagcca cctcaagaga aggctcacga tggtggccgc tactaccggg    1380
ctgatgatgc caatgtggtt cgtgaccgtg acctcgaggt ggacaccacc ctcaagagcc    1440
tgagccagca gatcgagaac atccggagcc cagagggaag ccgcaagaac ccgccccgca    1500
cctgccgtga cctcaagatg tgccactctg actggaagag tggagagtac tggattgacc    1560
ccaaccaagg ctgcaacctg gatgccatca agtcttctg caacatggag actggtgaga    1620
cctgcgtgta ccccactcag cccagtgtgg cccagaagaa ctggtacatc agcaagaacc    1680
ccaaggacaa gaggcatgtc tggttcggcg agagcatgac cgatggattc cagttcgagt    1740
atggcggcca gggctccgac cctgccgatg tggccatcca gctgaccttc ctgcgcctga    1800
tgtccaccga ggcctcccag aacatcacct accactgcaa gaacagcgtg gcctacatgg    1860
accagcagac tggcaacctc aagaaggcct tgctcctcaa gggctccaac gagatcgaga    1920
tccgcgccga gggcaacagc cgcttcacct acagcgtcac tgtcgatggc tgcacgagtc    1980
acaccggagc ctggggcaag acagtgattg aatacaaaac caccaagtcc tccgcctgc    2040 ccatcatcga tgtggccccc ttggacgttg gtgccccaga ccaggaattc ggcttcgacg    2100
ttggccctgt ctgcttcctg taaactccct ccatctaga                          2139
```

<210> SEQ ID NO 14
<211> LENGTH: 699
<212> TYPE: PRT
<213> ORGANISM: Artificial
<220> FEATURE:
<223> OTHER INFORMATION: CD4-TO Fusion Polypeptide

```
<400> SEQUENCE: 14

Met Asn Arg Gly Val Pro Phe Arg His Leu Leu Val Leu Gln Leu
 1               5                  10                  15

Ala Leu Leu Pro Ala Ala Thr Gln Gly Lys Lys Val Leu Gly Lys
             20                  25                  30

Lys Gly Asp Thr Val Glu Leu Thr Cys Thr Ala Ser Gln Lys Lys Ser
             35                  40                  45

Ile Gln Phe His Trp Lys Asn Ser Asn Gln Ile Lys Ile Leu Gly Asn
     50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                 85                  90                  95

Lys Asn Leu Lys Ile Glu Asp Ser Asp Thr Tyr Ile Cys Glu Val Glu
                100                 105                 110

Asp Gln Lys Glu Glu Val Gln Leu Leu Val Phe Gly Leu Thr Ala Asn
                115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
                180                 185                 190

Val Glu Phe Lys Ile Asp Ile Val Val Leu Ala Phe Gln Lys Ala Ser
                195                 200                 205

Ser Ile Val Tyr Lys Lys Glu Gly Glu Gln Val Glu Phe Ser Phe Pro
    210                 215                 220

Leu Ala Phe Thr Val Glu Lys Leu Thr Gly Ser Gly Glu Leu Trp Trp
225                 230                 235                 240

Gln Ala Glu Arg Ala Ser Ser Ser Lys Ser Trp Ile Thr Phe Asp Leu
                245                 250                 255

Lys Asn Lys Glu Val Ser Val Lys Arg Val Thr Gln Asp Pro Lys Leu
                260                 265                 270

Gln Met Gly Lys Lys Leu Pro Leu His Leu Thr Leu Pro Gln Ala Leu
                275                 280                 285

Pro Gln Tyr Ala Gly Ser Gly Asn Leu Thr Leu Ala Leu Glu Ala Lys
    290                 295                 300

Thr Gly Lys Leu His Gln Glu Val Asn Leu Val Val Met Arg Ala Thr
305                 310                 315                 320

Gln Leu Gln Lys Asn Leu Thr Cys Glu Val Trp Gly Pro Thr Ser Pro
                325                 330                 335

Lys Leu Met Leu Ser Leu Lys Leu Glu Asn Lys Glu Ala Lys Val Ser
                340                 345                 350

Lys Arg Glu Lys Ala Val Trp Val Leu Asn Pro Glu Ala Gly Met Trp
                355                 360                 365

Gln Cys Leu Leu Ser Asp Ser Gly Gln Val Leu Leu Glu Ser Asn Ile
    370                 375                 380

Lys Val Leu Pro Arg Ser Asn Gly Leu Pro Gly Pro Ile Gly Pro Pro
385                 390                 395                 400

Gly Pro Arg Gly Arg Thr Gly Asp Ala Gly Pro Val Gly Pro Pro Gly
                405                 410                 415
```

```
Pro Pro Gly Pro Pro Gly Pro Pro Gly Pro Pro Ser Ala Gly Phe Asp
            420                 425                 430
Phe Ser Phe Leu Pro Gln Pro Pro Gln Glu Lys Ala His Asp Gly Gly
        435                 440                 445
Arg Tyr Tyr Arg Ala Asp Ala Asn Val Val Arg Asp Arg Asp Leu
    450                 455                 460
Glu Val Asp Thr Thr Leu Lys Ser Leu Ser Gln Gln Ile Glu Asn Ile
465                 470                 475                 480
Arg Ser Pro Glu Gly Ser Arg Lys Asn Pro Ala Arg Thr Cys Arg Asp
            485                 490                 495
Leu Lys Met Cys His Ser Asp Trp Lys Ser Gly Glu Tyr Trp Ile Asp
            500                 505                 510
Pro Asn Gln Gly Cys Asn Leu Asp Ala Ile Lys Val Phe Cys Asn Met
            515                 520                 525
Glu Thr Gly Glu Thr Cys Val Tyr Pro Thr Gln Pro Ser Val Ala Gln
            530                 535                 540
Lys Asn Trp Tyr Ile Ser Lys Asn Pro Lys Asp Lys Arg His Val Trp
545                 550                 555                 560
Phe Gly Glu Ser Met Thr Asp Gly Phe Gln Phe Glu Tyr Gly Gly Gln
                565                 570                 575
Gly Ser Asp Pro Ala Asp Val Ala Ile Gln Leu Thr Phe Leu Arg Leu
            580                 585                 590
Met Ser Thr Glu Ala Ser Gln Asn Ile Thr Tyr His Cys Lys Asn Ser
            595                 600                 605
Val Ala Tyr Met Asp Gln Gln Thr Gly Asn Leu Lys Lys Ala Leu Leu
            610                 615                 620
Leu Lys Gly Ser Asn Glu Ile Glu Ile Arg Ala Glu Gly Asn Ser Arg
625                 630                 635                 640
Phe Thr Tyr Ser Val Thr Val Asp Gly Cys Thr Ser His Thr Gly Ala
                645                 650                 655
Trp Gly Lys Thr Val Ile Glu Tyr Lys Thr Thr Lys Ser Ser Arg Leu
            660                 665                 670
Pro Ile Ile Asp Val Ala Pro Leu Asp Val Gly Ala Pro Asp Gln Glu
            675                 680                 685
Phe Gly Phe Asp Val Gly Pro Val Cys Phe Leu
            690                 695

<210> SEQ ID NO 15
<211> LENGTH: 1947
<212> TYPE: DNA
<213> ORGANISM: Artificial
<220> FEATURE:
<221> NAME/KEY: CDS
<222> LOCATION: (24)...(1931)
<223> OTHER INFORMATION: Nucleotide Sequence Encoding CD4-T2 Fusion
      Polypeptide

<400> SEQUENCE: 15
aagcttccct cggcaaggcc acaatgaacc ggggagtccc ttttaggcac ttgcttctgg     60
tgctgcaact ggcgctcctc ccagcagcca ctcaggaaaa gaaagtggtg ctgggcaaaa    120
aaggggatac agtggaactg acctgtacag cttcccagaa gaagagcata caattccact    180
ggaaaaactc caaccagata aagattctgg gaaatcaggg ctccttctta actaaaggtc    240
catccaagct gaatgatcgc gctgactcaa gaagaagcct tgggaccaa ggaaactttc     300 ccctgatcat caagaatctt aagatagaag actcagatac ttacatctgt gaagtggagg    360
```

-continued

| | |
|---|---|
| accagaagga ggaggtgcaa ttgctagtgt tcggattgac tgccaactct gacacccacc | 420 |
| tgcttcaggg gcagagcctg accctgacct tggagagccc cctggtagt agcccctcag | 480 |
| tgcaatgtag gagtccaagg ggtaaaaaca tacagggggg gaagaccctc tccgtgtctc | 540 |
| agctggagct ccaggatagt ggcacctgga catgcactgt cttgcagaac cagaagaagg | 600 |
| tggagttcaa aatagacatc gtggtgctag cttttccagaa ggcctccagc atagtctata | 660 |
| agaaagaggg ggaacaggtg gagttctcct tcccactcgc ctttacagtt gaaaagctga | 720 |
| cgggcagtgg cgagctgtgg tggcaggcgg agagggcttc ctcctccaag tcttggatca | 780 |
| cctttgacct gaagaacaag gaagtgtctg taaaacgggt tacccaggac cctaagctcc | 840 |
| agatgggcaa gaagctcccg ctccacctca ccctgcccca ggccttgcct cagtatgctg | 900 |
| gctctggaaa cctcaccctg gcccttgaag cgaaaacagg aaagttgcat caggaagtga | 960 |
| acctggtggt gatgagagcc actcagctcc agaaaaattt gacctgtgag gtgtggggac | 1020 |
| ccacctcccc taagctgatg ctgagcttga aactggagaa caaggaggca aaggtctcga | 1080 |
| agcgggagaa ggcggtgtgg gtgctgaacc ctgaggcggg gatgtggcag tgtctgctga | 1140 |
| gtgactcggg acaggtcctg ctggaatcca acatcaaggt tctgcccaga tctgatgcca | 1200 |
| atgtggttcg tgaccgtgac ctcgaggtgg acaccaccct caagagcctg agccagcaga | 1260 |
| tcgagaacat ccggagccca gagggaagcc gcaagaaccc cgcccgcacc tgccgtgacc | 1320 |
| tcaagatgtg ccactctgac tggaagagtg gagagtactg gattgacccc aaccaaggct | 1380 |
| gcaacctgga tgccatcaaa gtcttctgca acatggagac tggtgagacc tgcgtgtacc | 1440 |
| ccactcagcc cagtgtggcc cagaagaact ggtacatcag caagaacccc aaggacaaga | 1500 |
| ggcatgtctg gttcggcgag agcatgaccg atggattcca gttcgagtat ggcggccagg | 1560 |
| gctccgaccc tgccgatgtg gccatccagc tgaccttcct gcgcctgatg tccaccgagg | 1620 |
| cctcccagaa catcacctac cactgcaaga acagcgtggc ctacatggac agcagactg | 1680 |
| gcaacctcaa gaaggccctg ctcctcaagg ctccaacga atcgagatc cgcgccgagg | 1740 |
| gcaacagccg cttcacctac agcgtcactg tcgatggctg cacgagtcac accggagcct | 1800 |
| ggggcaagac agtgattgaa tacaaaaacca ccaagtcctc ccgcctgccc atcatcgatg | 1860 |
| tggcccccctt ggacgttggt gccccagacc aggaattcgg cttcgacgtt ggccctgtct | 1920 |
| gcttcctgta aactccctcc atctaga | 1947 |

<210> SEQ ID NO 16
<211> LENGTH: 635
<212> TYPE: PRT
<213> ORGANISM: Artificial
<220> FEATURE:
<223> OTHER INFORMATION: CD4-T2 Fusion Polypeptide

<400> SEQUENCE: 16

Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
                20                  25                  30

Lys Gly Asp Thr Val Glu Leu Thr Cys Thr Ala Ser Gln Lys Lys Ser
            35                  40                  45

Ile Gln Phe His Trp Lys Asn Ser Asn Gln Ile Lys Ile Leu Gly Asn
        50                  55                  60

Gln Gly Ser Phe Leu Thr Lys Gly Pro Ser Lys Leu Asn Asp Arg Ala
65                  70                  75                  80

-continued

```
Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
        115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
            165                 170                 175

Gln Asp Ser Gly Thr Trp Thr Cys Thr Val Leu Gln Asn Gln Lys Lys
        180                 185                 190

Val Glu Phe Lys Ile Asp Ile Val Val Leu Ala Phe Gln Lys Ala Ser
    195                 200                 205

Ser Ile Val Tyr Lys Lys Glu Gly Glu Gln Val Glu Phe Ser Phe Pro
210                 215                 220

Leu Ala Phe Thr Val Glu Lys Leu Thr Gly Ser Gly Glu Leu Trp Trp
225                 230                 235                 240

Gln Ala Glu Arg Ala Ser Ser Ser Lys Ser Trp Ile Thr Phe Asp Leu
            245                 250                 255

Lys Asn Lys Glu Val Ser Val Lys Arg Val Thr Gln Asp Pro Lys Leu
        260                 265                 270

Gln Met Gly Lys Lys Leu Pro Leu His Leu Thr Leu Pro Gln Ala Leu
    275                 280                 285

Pro Gln Tyr Ala Gly Ser Gly Asn Leu Thr Leu Ala Leu Glu Ala Lys
290                 295                 300

Thr Gly Lys Leu His Gln Glu Val Asn Leu Val Val Met Arg Ala Thr
305                 310                 315                 320

Gln Leu Gln Lys Asn Leu Thr Cys Glu Val Trp Gly Pro Thr Ser Pro
            325                 330                 335

Lys Leu Met Leu Ser Leu Lys Leu Glu Asn Lys Glu Ala Lys Val Ser
        340                 345                 350

Lys Arg Glu Lys Ala Val Trp Val Leu Asn Pro Glu Ala Gly Met Trp
    355                 360                 365

Gln Cys Leu Leu Ser Asp Ser Gly Gln Val Leu Leu Glu Ser Asn Ile
370                 375                 380

Lys Val Leu Pro Arg Ser Asp Ala Asn Val Val Arg Asp Arg Asp Leu
385                 390                 395                 400

Glu Val Asp Thr Thr Leu Lys Ser Leu Ser Gln Gln Ile Glu Asn Ile
            405                 410                 415

Arg Ser Pro Glu Gly Ser Arg Lys Asn Pro Ala Arg Thr Cys Arg Asp
        420                 425                 430

Leu Lys Met Cys His Ser Asp Trp Lys Ser Gly Glu Tyr Trp Ile Asp
    435                 440                 445

Pro Asn Gln Gly Cys Asn Leu Asp Ala Ile Lys Val Phe Cys Asn Met
450                 455                 460

Glu Thr Gly Glu Thr Cys Val Tyr Pro Thr Gln Pro Ser Val Ala Gln
465                 470                 475                 480

Lys Asn Trp Tyr Ile Ser Lys Asn Pro Lys Asp Lys Arg His Val Trp
            485                 490                 495
```

-continued

```
Phe Gly Glu Ser Met Thr Asp Gly Phe Gln Phe Glu Tyr Gly Gly Gln
            500                 505                 510

Gly Ser Asp Pro Ala Asp Val Ala Ile Gln Leu Thr Phe Leu Arg Leu
        515                 520                 525

Met Ser Thr Glu Ala Ser Gln Asn Ile Thr Tyr His Cys Lys Asn Ser
    530                 535                 540

Val Ala Tyr Met Asp Gln Gln Thr Gly Asn Leu Lys Lys Ala Leu Leu
545                 550                 555                 560

Leu Lys Gly Ser Asn Glu Ile Glu Ile Arg Ala Glu Gly Asn Ser Arg
                565                 570                 575

Phe Thr Tyr Ser Val Thr Val Asp Gly Cys Thr Ser His Thr Gly Ala
            580                 585                 590

Trp Gly Lys Thr Val Ile Glu Tyr Lys Thr Thr Lys Ser Ser Arg Leu
        595                 600                 605

Pro Ile Ile Asp Val Ala Pro Leu Asp Val Gly Ala Pro Asp Gln Glu
    610                 615                 620

Phe Gly Phe Asp Val Gly Pro Val Cys Phe Leu
625                 630                 635
```

```
<210> SEQ ID NO 17
<211> LENGTH: 754
<212> TYPE: DNA
<213> ORGANISM: Homo sapiens
<220> FEATURE:
<221> NAME/KEY: CDS
<222> LOCATION: (1)...(738)

<400> SEQUENCE: 17
agatctgaac caatggattt caaaatcaac accgatgaga ttatgacttc actcaagtct      60
gttaatggac aaatagaaag cctcattagt cctgatggtt ctcgtaaaaa ccccgctaga     120
aactgcagag acctgaaatt ctgccatcct gaactcaaga gtggagaata ctgggttgac     180
cctaaccaag gatgcaaatt ggatgctatc aaggtattct gtaatatgga aactggggaa     240
acatgcataa gtgccaatcc tttgaatgtt ccacggaaac actggtggac agattctagt     300
gctgagaaga aacacgtttg gtttggagag tccatggatg gtggttttca gtttagctac     360
ggcaatcctg aacttcctga gatgtccttg atgtgcagc tggcattcct tcgacttctc     420
tccagccgag cttcccagaa catcacatat cactgcaaaa atagcattgc atacatggat     480
caggccagtg gaaatgtaaa gaaggccctg aagctgatgg ggtcaaatga aggtgaattc     540
aaggctgaag gaaatagcaa attcacctac acagttctgg aggatggttg cacgaaacac     600
actggggaat ggagcaaaac agtctttgaa tatcgaacac gcaaggctgt gagactacct     660
attgtagata ttgcacccta tgacattggt ggtcctgatc aagaatttgg tgtggacgtt     720
ggccctgttt gcttttata aaccaaactc taga                                  754
```

```
<210> SEQ ID NO 18
<211> LENGTH: 246
<212> TYPE: PRT
<213> ORGANISM: Homo sapiens

<400> SEQUENCE: 18

Arg Ser Glu Pro Met Asp Phe Lys Ile Asn Thr Asp Glu Ile Met Thr
1               5                   10                  15

Ser Leu Lys Ser Val Asn Gly Gln Ile Glu Ser Leu Ile Ser Pro Asp
            20                  25                  30
```

```
Gly Ser Arg Lys Asn Pro Ala Arg Asn Cys Arg Asp Leu Lys Phe Cys
         35                  40                  45
His Pro Glu Leu Lys Ser Gly Glu Tyr Trp Val Asp Pro Asn Gln Gly
 50                  55                  60
Cys Lys Leu Asp Ala Ile Lys Val Phe Cys Asn Met Glu Thr Gly Glu
 65                  70                  75                  80
Thr Cys Ile Ser Ala Asn Pro Leu Asn Val Pro Arg Lys His Trp Trp
                 85                  90                  95
Thr Asp Ser Ser Ala Glu Lys Lys His Val Trp Phe Gly Glu Ser Met
                100                 105                 110
Asp Gly Gly Phe Gln Phe Ser Tyr Gly Asn Pro Glu Leu Pro Glu Asp
            115                 120                 125
Val Leu Asp Val Gln Leu Ala Phe Leu Arg Leu Leu Ser Ser Arg Ala
130                 135                 140
Ser Gln Asn Ile Thr Tyr His Cys Lys Asn Ser Ile Ala Tyr Met Asp
145                 150                 155                 160
Gln Ala Ser Gly Asn Val Lys Lys Ala Leu Lys Leu Met Gly Ser Asn
                165                 170                 175
Glu Gly Glu Phe Lys Ala Glu Gly Asn Ser Lys Phe Thr Tyr Thr Val
            180                 185                 190
Leu Glu Asp Gly Cys Thr Lys His Thr Gly Glu Trp Ser Lys Thr Val
        195                 200                 205
Phe Glu Tyr Arg Thr Arg Lys Ala Val Arg Leu Pro Ile Val Asp Ile
    210                 215                 220
Ala Pro Tyr Asp Ile Gly Gly Pro Asp Gln Glu Phe Gly Val Asp Val
225                 230                 235                 240
Gly Pro Val Cys Phe Leu
                245

<210> SEQ ID NO 19
<211> LENGTH: 1536
<212> TYPE: DNA
<213> ORGANISM: Artificial
<220> FEATURE:
<221> NAME/KEY: CDS
<222> LOCATION: (18)...(1523)
<223> OTHER INFORMATION: Nucleotide Sequence Encoding sTNF-RII-T3 Fusion
      Polypeptide

<400> SEQUENCE: 19
ggatcccgcc cgcacccatg cgcccgtcg ccgtctgggc cgcgctggcc gtcggactgg      60
agctctgggc tgcggcgcac gccttgcccg cccaggtggc atttacaccc tacgccccgg    120
agcccgggag cacatgccgg ctcagagaat actatgacca gacagctcag atgtgctgca    180
gcaaatgctc gccgggccaa catgcaaaag tcttctgtac aagacctcg gacaccgtgt     240 gtgactcctg tgaggacagc acatacaccc agctctggaa ctgggttccc gagtgcttga    300
gctgtggctc ccgctgtagc tctgaccagg tggaaactca agcctgcact cgggaacaga    360
accgcatctg cacctgcagg cccggctggt actgcgcgct gagcaagcag gagggtgcc     420 ggctgtgcgc gccgctgcgc aagtgccgcc cgggcttcgg cgtggccaga ccaggaactg    480
aaacatcaga cgtggtgtgc aagccctgtg ccccggggac gttctccaac acgacttcat    540
ccacggatat ttgcaggccc caccagatct gtaacgtggt ggccatccct gggaatgcaa    600
gcatggatgc agtctgcacg tccacgtccc ccacccggag tatggccca ggggcagtac     660 acttaccca gccagtgtcc acacgatccc aacacacgca gccaactcca gaacccagca    720
```

```
ctgctccaag cacctccttc ctgctcccaa tgggccccag cccccagct gaagggagca    780 ctggatctga accaatggat ttcaaaatca acaccgatga gattatgact tcactcaagt    840
ctgttaatgg acaaatagaa agcctcatta gtcctgatgg ttctcgtaaa aaccccgcta    900
gaaactgcag agacctgaaa ttctgccatc ctgaactcaa gagtggagaa tactgggttg    960
accctaacca aggatgcaaa ttggatgcta tcaaggtatt ctgtaatatg gaaactgggg   1020
aaacatgcat aagtgccaat cctttgaatg ttccacggaa acactggtgg acagattcta   1080
gtgctgagaa gaaacacgtt tggtttggag agtccatgga tggtggtttt cagtttagct   1140
acggcaatcc tgaacttcct gaagatgtcc ttgatgtgca gctggcattc cttcgacttc   1200
tctccagccg agcttcccag aacatcacat atcactgcaa aaatagcatt gcatacatgg   1260
atcaggccag tggaaatgta aagaaggccc tgaagctgat ggggtcaaat gaaggtgaat   1320
tcaaggctga aggaaatagc aaattcacct acacagttct ggaggatggt tgcacgaaac   1380
acactgggga atggagcaaa acagtctttg aatatcgaac acgcaaggct gtgagactac   1440
ctattgtaga tattgcaccc tatgacattg gtggtcctga tcaagaattt ggtgtggacg   1500
ttggccctgt ttgctttta taaaccaaac tctaga                              1536
```

<210> SEQ ID NO 20
<211> LENGTH: 501
<212> TYPE: PRT
<213> ORGANISM: Artificial
<220> FEATURE:
<223> OTHER INFORMATION: sTNF-RII-T3 Fusion Polypeptide

<400> SEQUENCE: 20

```
Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
                20                  25                  30

Ala Pro Glu Pro Gly Ser Thr Cys Arg Leu Arg Glu Tyr Tyr Asp Gln
            35                  40                  45

Thr Ala Gln Met Cys Cys Ser Lys Cys Ser Pro Gly Gln His Ala Lys
        50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220
```

-continued

```
Gln His Thr Gln Pro Thr Pro Glu Pro Ser Thr Ala Pro Ser Thr Ser
225                 230                 235                 240

Phe Leu Leu Pro Met Gly Pro Ser Pro Pro Ala Glu Gly Ser Thr Gly
                245                 250                 255

Ser Glu Pro Met Asp Phe Lys Ile Asn Thr Asp Glu Ile Met Thr Ser
                260                 265                 270

Leu Lys Ser Val Asn Gly Gln Ile Glu Ser Leu Ile Ser Pro Asp Gly
            275                 280                 285

Ser Arg Lys Asn Pro Ala Arg Asn Cys Arg Asp Leu Lys Phe Cys His
        290                 295                 300

Pro Glu Leu Lys Ser Gly Glu Tyr Trp Val Asp Pro Asn Gln Gly Cys
305                 310                 315                 320

Lys Leu Asp Ala Ile Lys Val Phe Cys Asn Met Glu Thr Gly Glu Thr
                325                 330                 335

Cys Ile Ser Ala Asn Pro Leu Asn Val Pro Arg Lys His Trp Trp Thr
                340                 345                 350

Asp Ser Ser Ala Glu Lys Lys His Val Trp Phe Gly Glu Ser Met Asp
            355                 360                 365

Gly Gly Phe Gln Phe Ser Tyr Gly Asn Pro Glu Leu Pro Glu Asp Val
        370                 375                 380

Leu Asp Val Gln Leu Ala Phe Leu Arg Leu Leu Ser Ser Arg Ala Ser
385                 390                 395                 400

Gln Asn Ile Thr Tyr His Cys Lys Asn Ser Ile Ala Tyr Met Asp Gln
                405                 410                 415

Ala Ser Gly Asn Val Lys Lys Ala Leu Lys Leu Met Gly Ser Asn Glu
            420                 425                 430

Gly Glu Phe Lys Ala Glu Gly Asn Ser Lys Phe Thr Tyr Thr Val Leu
        435                 440                 445

Glu Asp Gly Cys Thr Lys His Thr Gly Glu Trp Ser Lys Thr Val Phe
450                 455                 460

Glu Tyr Arg Thr Arg Lys Ala Val Arg Leu Pro Ile Val Asp Ile Ala
465                 470                 475                 480

Pro Tyr Asp Ile Gly Gly Pro Asp Gln Glu Phe Gly Val Asp Val Gly
                485                 490                 495

Pro Val Cys Phe Leu
                500
```